US012616614B2

(12) United States Patent     (10) Patent No.:   US 12,616,614 B2

Schneider et al.     (45) Date of Patent:     May 5, 2026

(54) ABSORBENT ARTICLES WITH CORRUGATED ELASTOMERIC LAMINATES AND METHODS FOR MAKING CORRUGATED ELASTOMERIC LAMINATES

(71) Applicant: The Procter & Gamble Company, Cincinnati, OH (US)

(72) Inventors: Uwe Schneider, Cincinnati, OH (US); Joseph Allen Eckstein, Sunman, IN (US); Todd Leon Mansfield, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 333 days.

(21) Appl. No.: 18/320,271

(22) Filed: May 19, 2023

(65) Prior Publication Data

US 2023/0390122 A1     Dec. 7, 2023

Related U.S. Application Data

(60) Provisional application No. 63/349,609, filed on Jun. 7, 2022.

(51) Int. Cl.

| | |
|---|---|
| *A61F 13/15* | (2006.01) |
| *B32B 3/30* | (2006.01) |
| *B32B 5/02* | (2006.01) |
| *B32B 7/05* | (2019.01) |
| *B32B 27/12* | (2006.01) |

(52) U.S. Cl.
CPC .. *A61F 13/15699* (2013.01); *A61F 13/15723* (2013.01); *A61F 13/15764* (2013.01); *B32B 3/30* (2013.01); *B32B 5/022* (2013.01); *B32B 7/05* (2019.01); *B32B 27/12* (2013.01); *A61F*

*2013/15715* (2013.01); *A61F 2013/15869* (2013.01); *A61F 2013/15878* (2013.01); *A61F 2013/1591* (2013.01); *B32B 2555/02* (2013.01)

(58) Field of Classification Search
CPC .......... A61F 13/15593; A61F 13/15699; A61F 13/15723; A61F 13/15764; A61F 13/4902; A61F 2013/15715; A61F 2013/15869; A61F 2013/15878; A61F 13/49019; A61F 2013/1591; A61F 2013/49025; B32B 2555/02; B32B 27/12; B32B 3/30; B32B 5/022; B32B 7/05
USPC ....... 156/60, 73.1, 73.2, 148, 160, 161, 163, 156/164, 166, 176, 178, 179, 196, 199, 156/205, 207, 208, 210, 212, 229, 290, 156/291, 292, 308.2, 309.6, 324
See application file for complete search history.

(56) References Cited

U.S. PATENT DOCUMENTS

| | | |
|---|---|---|
| 2010/0076394 A1 | 3/2010 | Hayase |
| 2017/0014277 A1 | 1/2017 | Matsui et al. |
| 2020/0039178 A1 | 2/2020 | Hidaka |

(Continued)

OTHER PUBLICATIONS

PCT Search Report and Written Opinion for PCT/US2023/024390 dated Sep. 12, 2023, 10 pages.

*Primary Examiner* — Marla D McConnell
(74) *Attorney, Agent, or Firm* — Gregory P. Habiak; Charles R. Matson

(57) ABSTRACT

The present disclosure relates to absorbent articles and methods for manufacturing absorbent articles, and elastomeric laminates and methods for making corrugated elastomeric laminates that may be used as components of absorbent articles.

19 Claims, 23 Drawing Sheets

(56) References Cited

U.S. PATENT DOCUMENTS

| | | | |
|---|---|---|---|
| 2021/0022411 A1* | 1/2021 | Li | ..................... A61F 13/49061 |
| 2021/0069029 A1* | 3/2021 | Sakai | ................ B29C 66/81433 |
| 2021/0100697 A1 | 4/2021 | Varona et al. | |

* cited by examiner

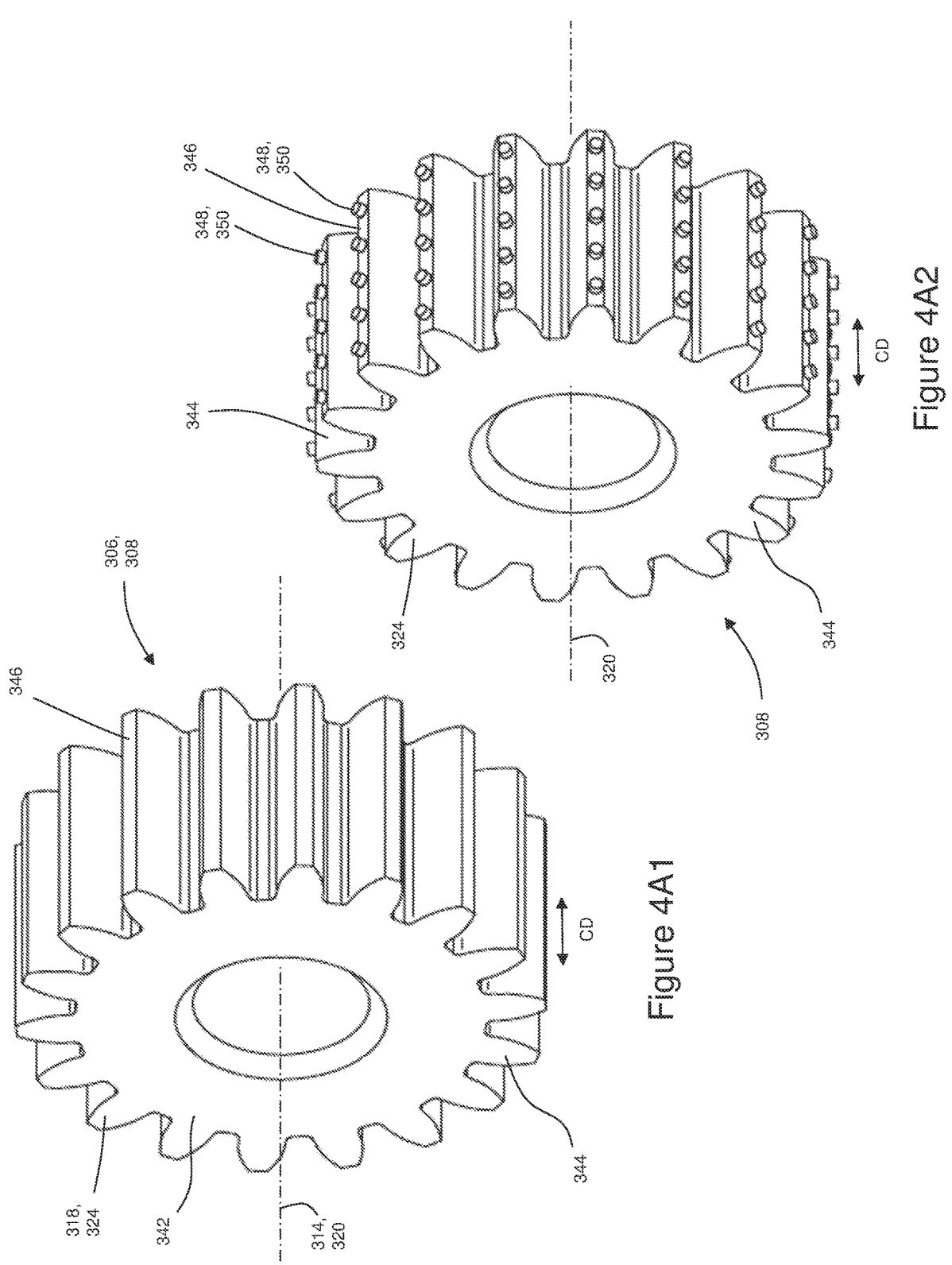
Figure 4A1
Figure 4A2

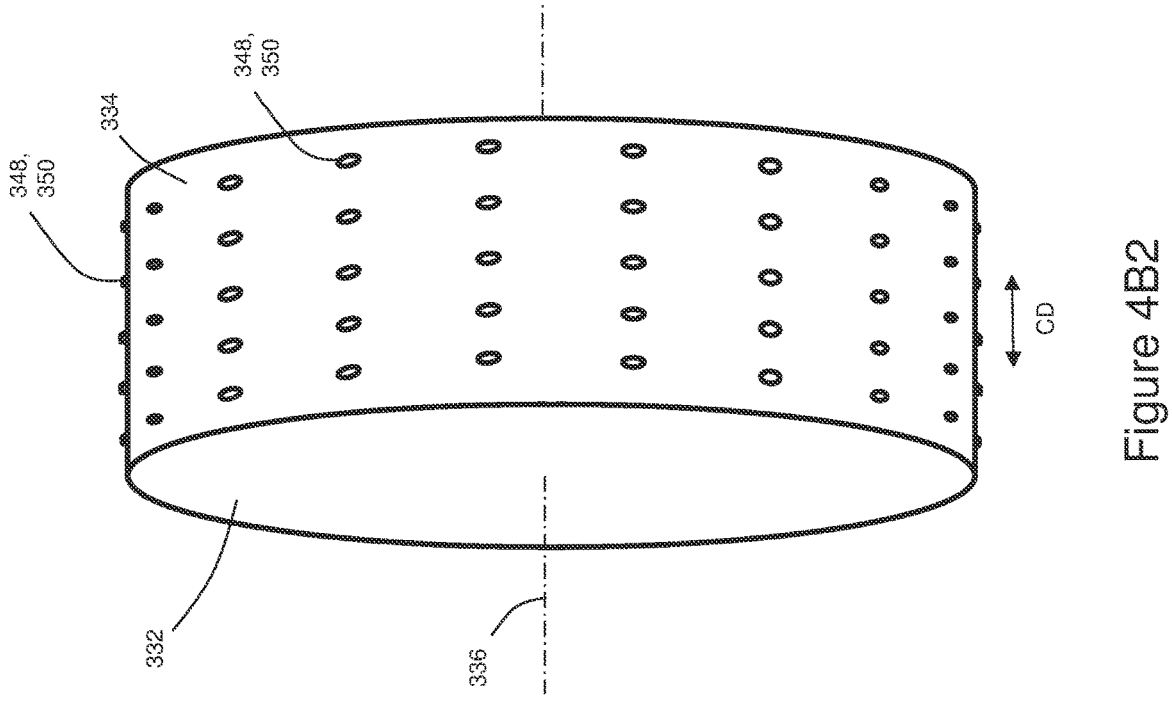
Figure 4B2
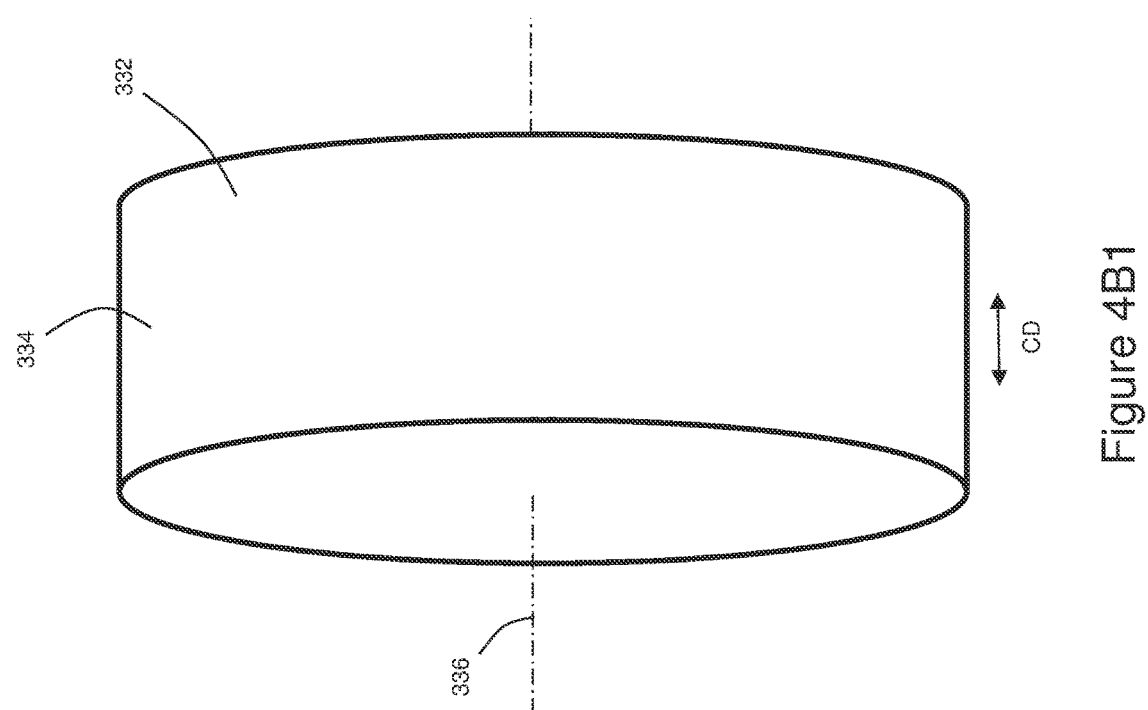
Figure 4B1

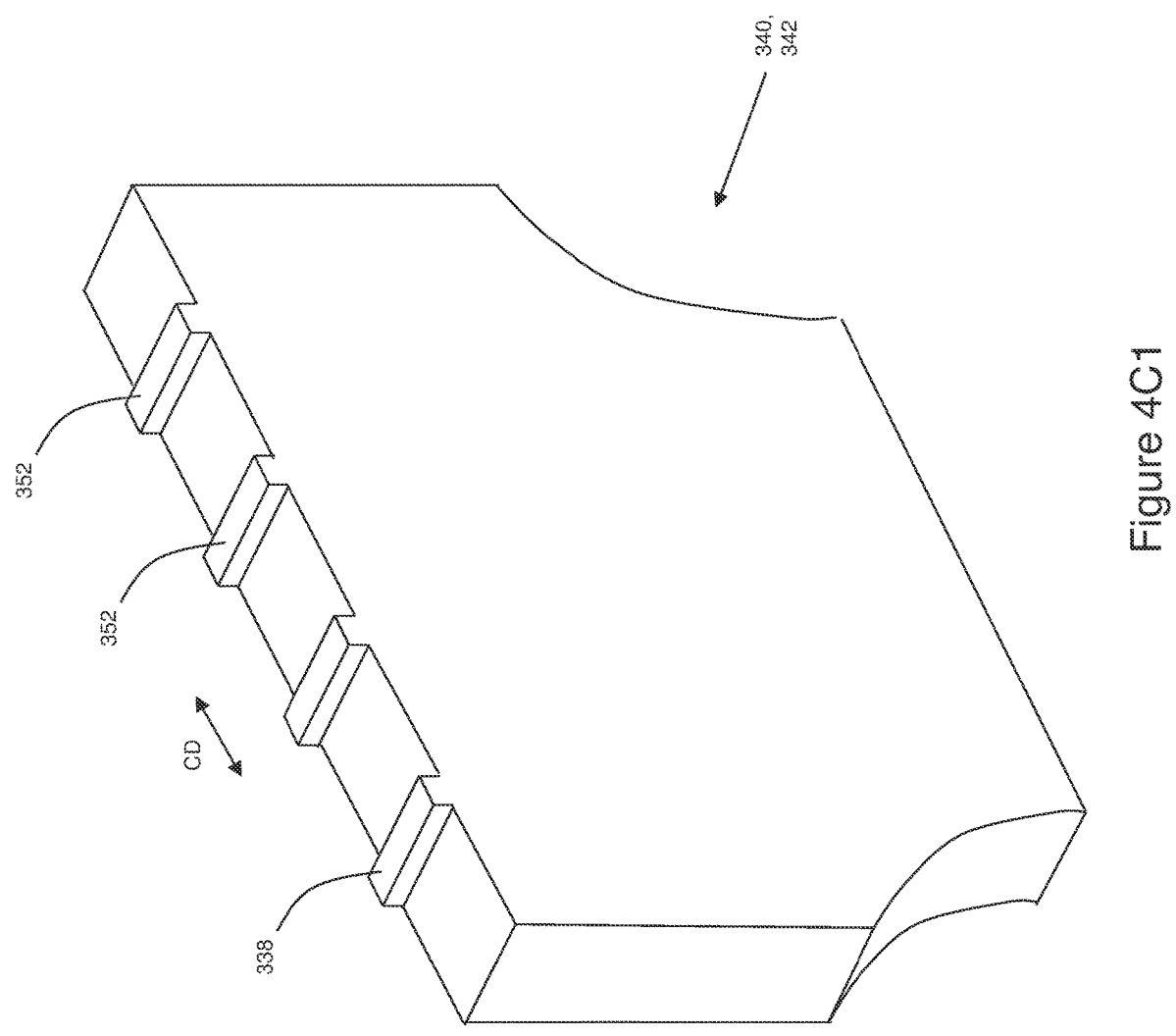
Figure 4C1

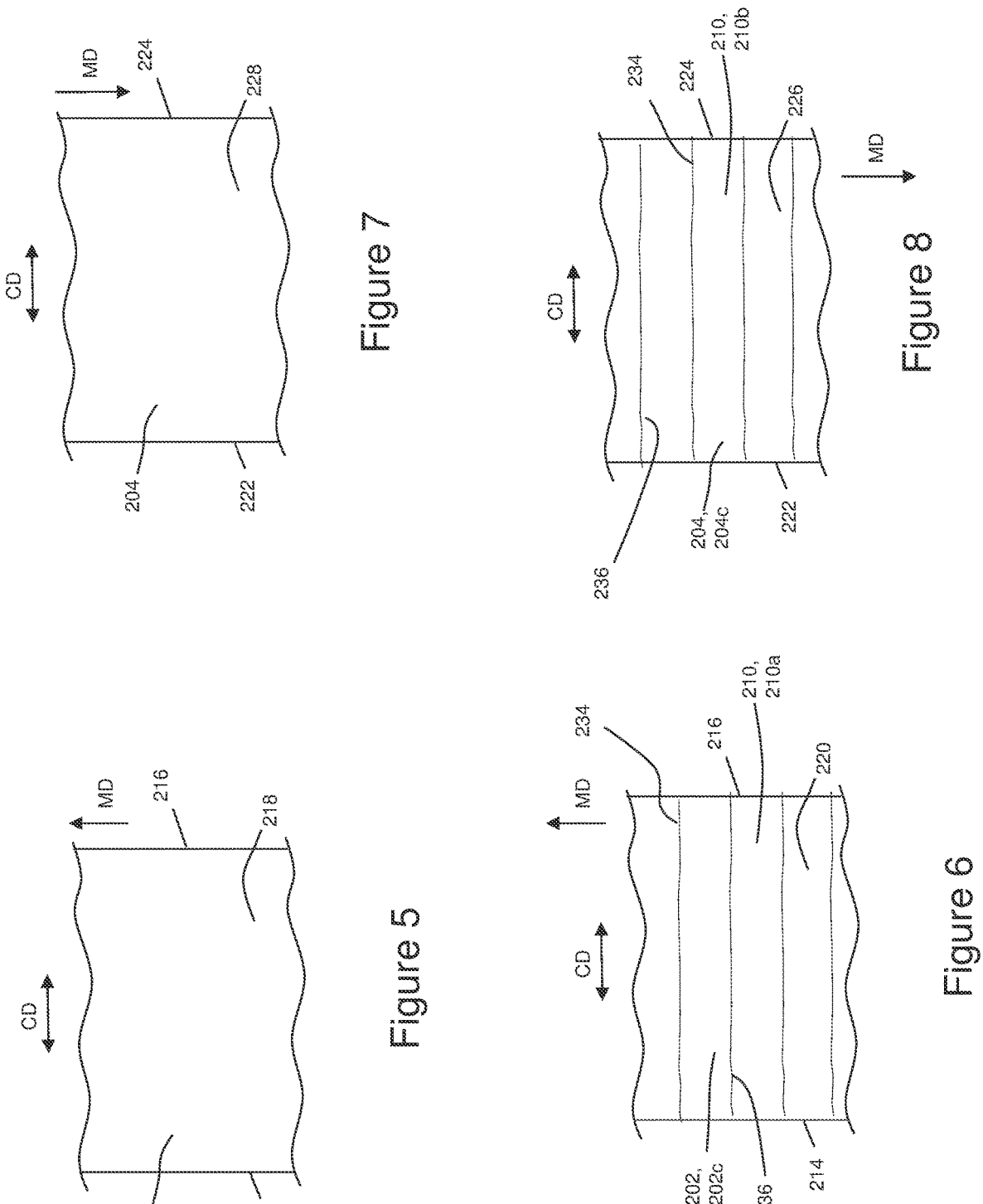

ABSORBENT ARTICLES WITH CORRUGATED ELASTOMERIC LAMINATES AND METHODS FOR MAKING CORRUGATED ELASTOMERIC LAMINATES

CROSS REFERENCE TO RELATED APPLICATIONS

This application claims the benefit of U.S. Provisional Application No. 63/349,609, filed Jun. 7, 2022, which is incorporated by reference herein in its entirety.

FIELD OF THE INVENTION

The present disclosure relates to absorbent articles and methods for manufacturing absorbent articles, and more particularly, to elastomeric laminates and methods for making corrugated elastomeric laminates that may be used as components of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from an advancing web or webs are combined with other individual components created from other advancing webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

Some absorbent articles have components that include elastic laminates. Such elastic laminates may include an elastic material bonded between two substrates. The elastic material may include an elastic film and/or elastic strands. In some laminates, two nonwovens may be deformed to create corrugations, and elastic strands are joined between two corrugated nonwovens while the elastic strands are in a stretched condition. As such, the nonwovens gather between the locations where the nonwovens are bonded to each other and the elastic strands. The resulting elastic laminate is stretchable to the extent that the corrugations allow the elastic strands to elongate. However, processes for assembling such laminates may utilize adhesives that are coated over the full length of the elastic strands to anchor the elastic strands and to connect the two nonwovens together. As such, relatively large amounts of adhesive may be utilized to help ensure attachment of the elastic strands to the corrugations. As a result, when the laminate is stretched at relatively high rates, the relatively large coating of adhesive may hinder the contraction rates of the elastics.

Consequently, it would be beneficial to provide elastic laminates and methods and apparatuses for producing such elastic laminates wherein the elastic strands may be bonded between corrugated substrates in desired locations so as to help reduce negative impacts on contraction rates of the laminates.

SUMMARY OF THE INVENTION

In one form, a method for making an elastomeric laminate comprises steps of: providing a first corrugated substrate by forming ridges that alternate with depressions along a machine direction in a first substrate; providing a second corrugated substrate by forming ridges that alternate with depressions along the machine direction in a second substrate; advancing elastic strands in the machine direction; stretching the elastic strands in the machine direction; subsequent to the step of stretching the elastic strands, applying a first adhesive intermittently to the elastic strands to form discrete regions of the first adhesive on the elastic strands; bonding discrete lengths of the elastic strands with and between the first corrugated substrate and the second corrugated substrate with first bonds formed with the discrete regions of the first adhesive; and bonding the depressions of first corrugated substrate directly with the depressions of the second corrugated substrate with second bonds along the machine direction between consecutive first bonds.

In another form, a method for making an elastomeric laminate comprises steps of: providing a first corrugated substrate by forming ridges that alternate with depressions along a machine direction in a first substrate; providing a second substrate, wherein the second substrate is not corrugated; advancing elastic strands in the machine direction; stretching the elastic strands in the machine direction; subsequent to stretching the elastics strands, applying a first adhesive intermittently to the elastic strands to form discrete regions of the first adhesive on the elastic strands; bonding discrete lengths of the elastic strands with and between the first corrugated substrate and the second substrate with first bonds formed with the discrete regions of the first adhesive; and bonding the depressions of first corrugated substrate directly with the second substrate with second bonds along the machine direction between consecutive first bonds.

In yet another form, a method for making an elastomeric laminate comprises steps of: providing a first substrate and a second substrate; corrugating at least one of the first substrate and the second substrate by forming ridges that alternate with depressions along a machine direction in at least one of the first substrate and the second substrate; advancing elastic strands in the machine direction; stretching the elastic strands in the machine direction; bonding discrete lengths of the elastic strands with and between the first substrate and the second substrate with first bonds; and bonding the first substrate directly with the second substrate with second bonds along the machine direction between consecutive first bonds.

In still another form, an elastomeric laminate comprises: a first substrate; a second substrate, wherein at least one of the first substrate and the second substrate is corrugated; elastic strands positioned between the first substrate and the second substrate; wherein discrete lengths of the elastic strands are bonded with the first substrate and the second substrate with first bonds; wherein the first substrate and the second substrate are bonded directly with each other with second bonds positioned between consecutive first bonds; and wherein the elastic strands extend through the second bonds and the elastic strands can retract and stretch through the second bonds.

BRIEF DESCRIPTION OF THE DRAWINGS

FIG. 4A1 is an isometric view of a corrugating roll.

FIG. 4A2 is an isometric view of a corrugating roll with bonding elements.

FIG. 4B1 is an isometric view of an anvil roll.

FIG. 4B2 is an isometric view of an anvil roll with bonding elements.

FIG. 4C1 is an isometric view of an ultrasonic horn with an energy transfer surface including raised lands.

FIG. 5 is a view of a first substrate taken along section 5-5 in FIGS. 4A, 4B, and 4C.

FIG. 6 is a view of the first substrate with corrugations taken along section 6-6 in FIGS. 4A, 4B, and 4C.

FIG. 7 is a view of a second substrate taken along section 7-7 in FIGS. 4A, 4B, and 4C.

FIG. 8 is a view of the second substrate with corrugations taken along section 8-8 in FIG. 4A.

DETAILED DESCRIPTION OF THE INVENTION

Figure 1A:
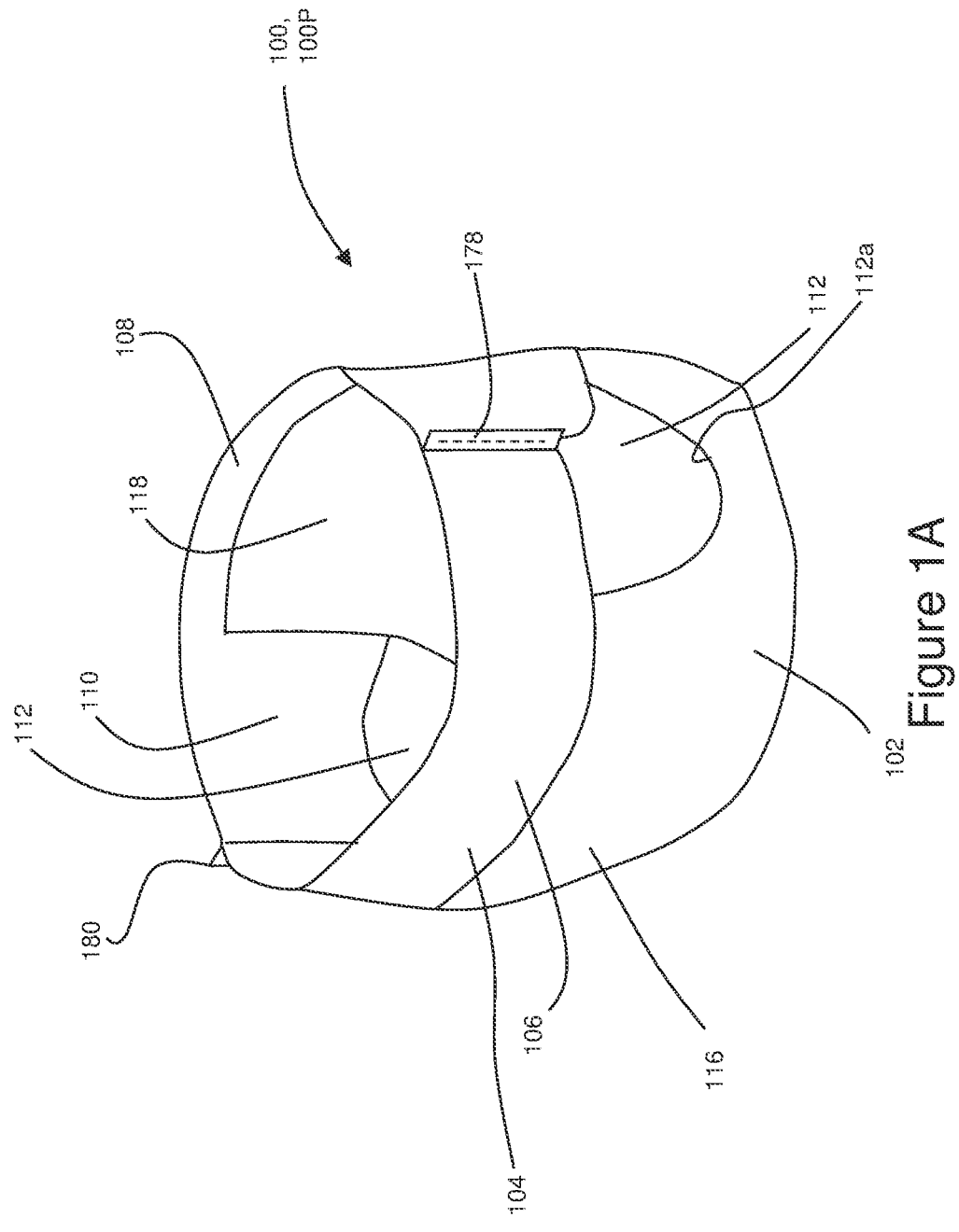
FIG. 1A is a front perspective view of a diaper pant.

The following term explanations may be useful in understanding the present disclosure:

"Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The terms "registration process," "registration system," "registration," "register," "registered," or "registering" as used herein refer to a machine control process or system for controlling a substrate or laminate, (which can have multiplicity of pre-produced objects, such as apertures, bonds, graphics, patterns, design elements, and/or insignia spaced on the substrate or laminate at a pitch interval that may vary in the machine direction) through a converting line producing articles, by providing a positional adjustment of the pre-produced objects on the substrate or laminate to a target position constant associated with a pitched unit operation of the converting line.

The term "substrate" is used herein to describe a material which is primarily two-dimensional (i.e., in an XY plane) and whose thickness (in a Z direction) is relatively small (i.e., $\frac{1}{10}$ or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674, 216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, all of which are incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,897,545; 5,957, 908; 6,120,487; 6,120,489; 7,569,039 and U.S. Patent Publication Nos. 2003/0233082 A1; 2005/0107764 A1, 2012/ 0061016 A1, 2012/0061015 A1; 2013/0255861 A1; 2013/ 0255862 A1; 2013/0255863 A1; 2013/0255864 A1; and 2013/0255865 A1, all of which are incorporated by reference herein.

The present disclosure relates to methods for manufacturing absorbent articles, and in particular, to elastic laminates and methods for making elastic laminates that may be used as components of absorbent articles. With regard to some assembly processes described herein, a first corrugated substrate is provided by forming ridges that alternate with depressions along a machine direction in a first substrate, and a second corrugated substrate is provided by forming ridges that alternate with depressions along the machine direction in a second substrate. Elastic strands are advanced and stretched in the machine direction. Subsequent to stretching the elastic strands, a first adhesive is intermittently applied to the elastic strands to form discrete regions of the first adhesive on the elastic strands. Discrete lengths of the elastic strands are bonded with and between the first corrugated substrate and the second corrugated substrate with first bonds formed with the discrete regions of the first adhesive. The depressions of first corrugated substrate are directly bonded with the depressions of the second corrugated substrate with second bonds along the machine direction between consecutive first bonds. In some assembly processes, one of the first and second substrates is corrugated and the other one of the first and second substrates is not corrugated. With regard to elastic laminates discussed herein, at least one of the first substrate and the second substrate is corrugated, and elastic strands are positioned between the first substrate and the second substrate. Discrete lengths of the elastic strands are bonded with the first substrate and the second substrate with first bonds, and the first substrate and the second substrate are bonded directly with each other with second bonds positioned between consecutive first bonds. The elastic strands extend through the second bonds and the elastic strands can retract and stretch through the second bonds.

Figure 1B:
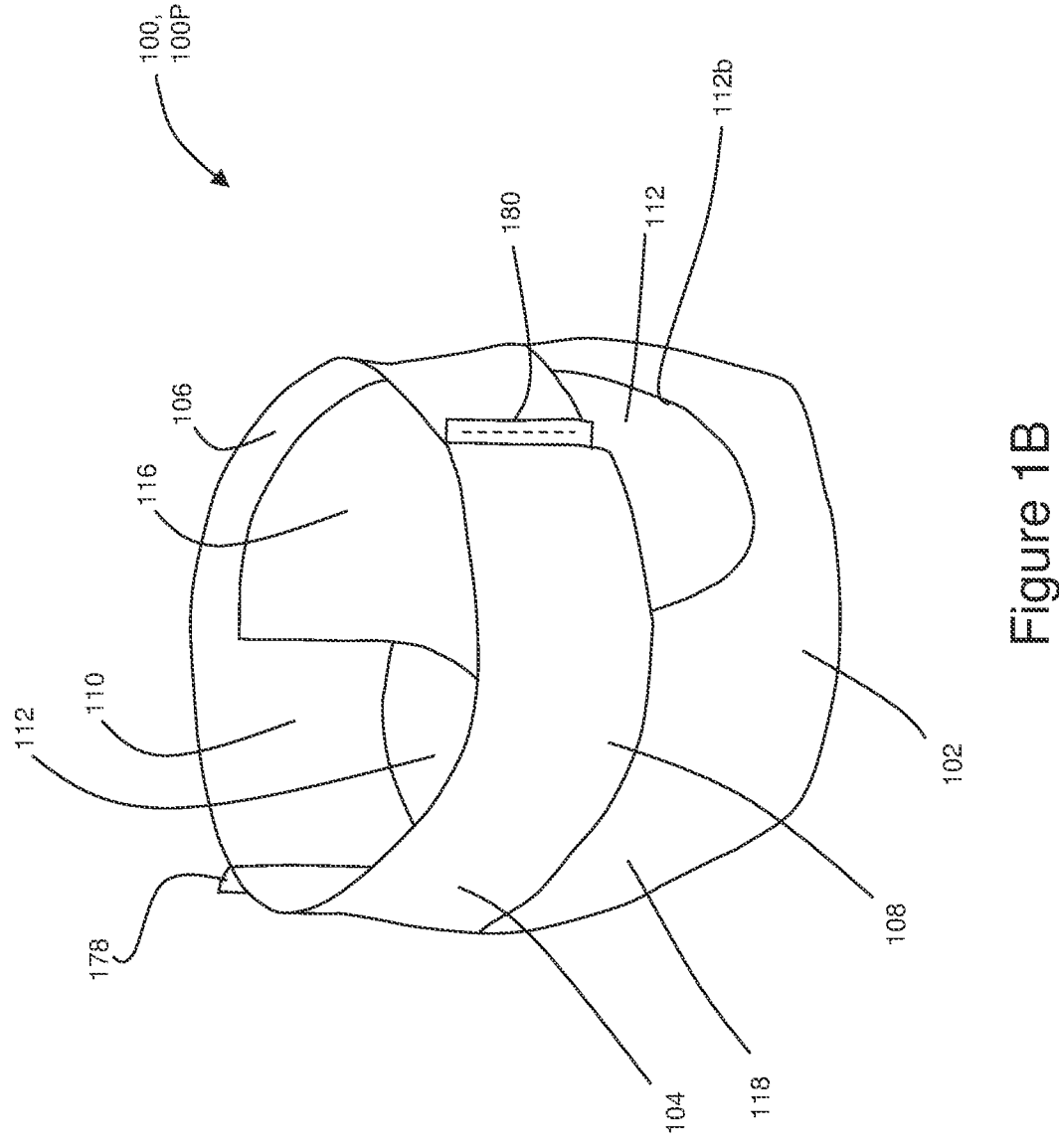
FIG. 1B is a rear perspective view of a diaper pant.
Figures 2, 3A, 3B:
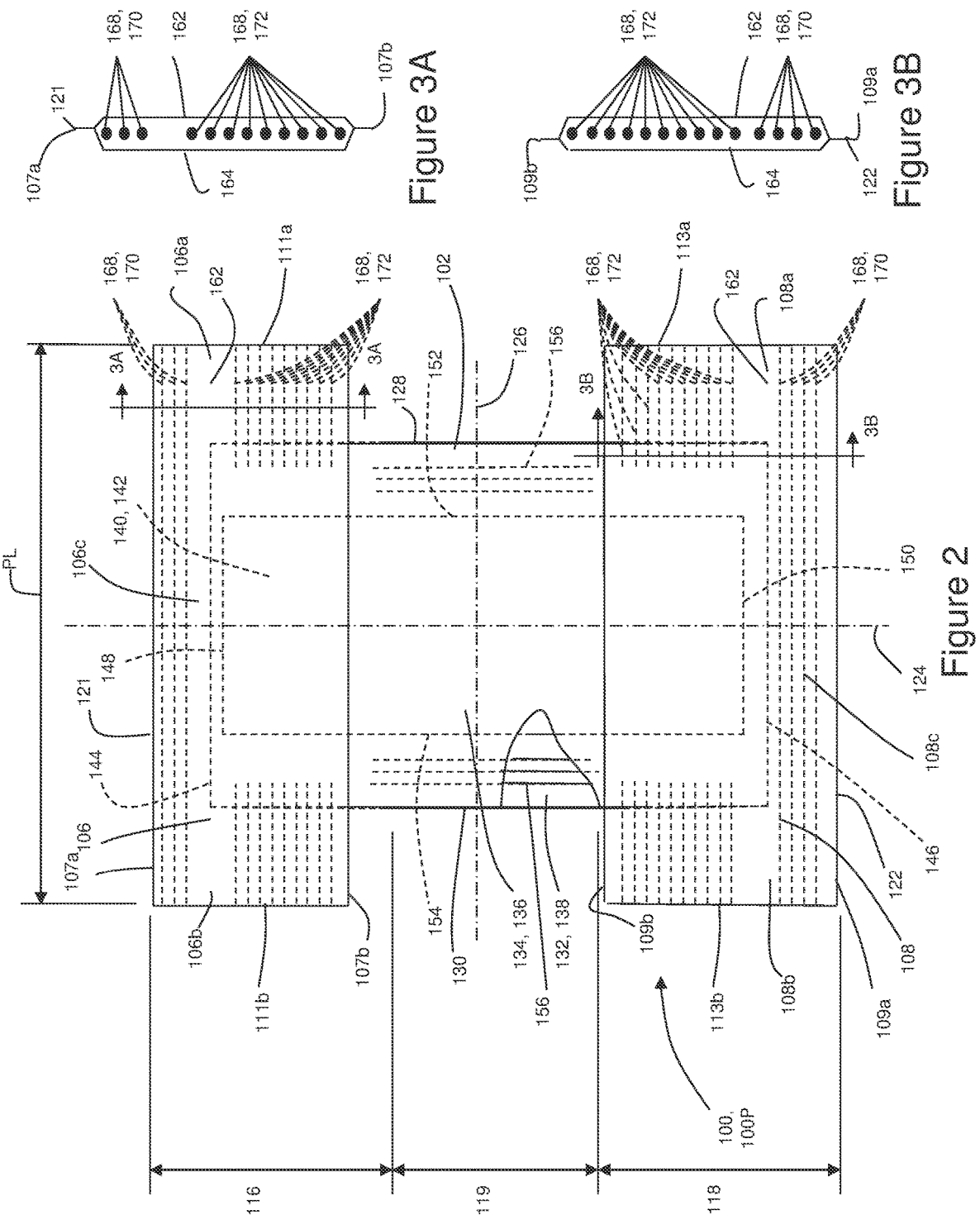
FIG. 2 is a partially cut away plan view of the diaper pant shown in FIGS. 1A and 1B in a flat, uncontracted state.
FIG. 3A is a cross-sectional view of the diaper pant of FIG. 2 taken along line 3A-3A.
FIG. 3B is a cross-sectional view of the diaper pant of FIG. 2 taken along line 3B-3B.

FIGS. 1A, 1B, and 2 show an example of an absorbent article 100 in the form of a diaper pant 100P that may include components constructed from elastic laminates assembled in accordance with the apparatuses and methods disclosed herein. In particular, FIGS. 1A and 1B show perspective views of a diaper pant 100P in a pre-fastened configuration, and FIG. 2 shows a plan view of the diaper pant 100P with the portion of the diaper that faces away from a wearer oriented toward the viewer. The diaper pant 100P includes a chassis 102 and a ring-like elastic belt 104. As discussed below in more detail, a first elastic belt 106 and a second elastic belt 108 are bonded together to form the ring-like elastic belt 104.

With continued reference to FIG. 2, the diaper pant 100P and the chassis 102 each include a first waist region 116, a second waist region 118, and a crotch region 119 disposed intermediate the first and second waist regions. The first waist region 116 may be configured as a front waist region, and the second waist region 118 may be configured as back waist region. The diaper 100P may also include a laterally extending front waist edge 121 in the front waist region 116 and a longitudinally opposing and laterally extending back waist edge 122 in the back waist region 118. To provide a frame of reference for the present discussion, the diaper 100P and chassis 102 of FIG. 2 are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1A, 1B, and 2, the diaper pant 100P may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100P may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2, the laterally extending end edges 144 and 146 are located longitudinally inward from the laterally extending front waist edge 121 in the front waist region 116 and the laterally extending back waist edge 122 in the back waist region 118. When the diaper pant 100P is worn on the lower torso of a wearer, the front waist edge 121 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

As previously mentioned, the diaper pant 100P may include a backsheet 136. The backsheet 136 may also define the outer surface 134 of the chassis 102. The backsheet 136 may also comprise a woven or nonwoven material, polymeric films such as thermoplastic films of polyethylene or polypropylene, and/or a multi-layer or composite materials comprising a film and a nonwoven material. The backsheet may also comprise an elastomeric film. An example backsheet 136 may be a polyethylene film having a thickness of from about 0.012 mm (0.5 mils) to about 0.051 mm (2.0 mils). Further, the backsheet 136 may permit vapors to escape from the absorbent core (i.e., the backsheet is breathable) while still preventing exudates from passing through the backsheet 136.

Also described above, the diaper pant 100P may include a topsheet 138. The topsheet 138 may also define all or part of the inner surface 132 of the chassis 102. The topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens; porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art. Topsheets 138 may be selected from high loft nonwoven topsheets, apertured film topsheets and apertured nonwoven topsheets. Exemplary apertured films may include those described in U.S. Pat. Nos. 5,628,097; 5,916,661; 6,545,197; and 6,107,539, all of which are incorporated by reference herein.

As mentioned above, the diaper pant 100P may also include an absorbent assembly 140 that is joined to the chassis 102. As shown in FIG. 2, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834, 735, all of which are incorporated by reference herein.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/ 0097895 A1, all of which are incorporated by reference herein.

As previously mentioned, the diaper 100P may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695, 278; 4,795,454; 4,704,115; 4,909,803; and U.S. Patent Publication No. 2009/0312730 A1, all of which are incorporated by reference herein.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIGS. 1A and 1B. The ring-like elastic belt may be formed by joining a first elastic belt to a second elastic belt with a permanent side seam or with an openable and reclosable fastening system disposed at or adjacent the laterally opposing sides of the belts.

As previously mentioned, the ring-like elastic belt 104 may be defined by a first elastic belt 106 connected with a second elastic belt 108. As shown in FIG. 2, the first elastic belt 106 extends between a first longitudinal side edge 111a and a second longitudinal side edge 111b and defines first and second opposing end regions 106a, 106b and a central region 106c. And the second elastic 108 belt extends between a first longitudinal side edge 113a and a second longitudinal side edge 113b and defines first and second opposing end regions 108a, 108b and a central region 108c. The distance between the first longitudinal side edge 111a and the second longitudinal side edge 111b defines the pitch length, PL, of the first elastic belt 106, and the distance between the first longitudinal side edge 113a and the second longitudinal side edge 113b defines the pitch length, PL, of the second elastic belt 108. The central region 106c of the first elastic belt is connected with the first waist region 116 of the chassis 102, and the central region 108c of the second elastic belt 108 is connected with the second waist region 118 of the chassis 102. As shown in FIGS. 1A and 1B, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer laterally extending edge 107a and an inner laterally extending edge 107b, and the second elastic belt 108 defines an outer laterally extending edge 109a and an inner laterally extending edge 109b. As such, a perimeter edge 112a of one leg opening may be defined by portions of the inner laterally extending edge 107b of the first elastic belt 106, the inner laterally extending edge 109b of the second elastic belt 108, and the first longitudinal or right side edge 128 of the chassis 102. And a perimeter edge 112b of the other leg opening may be defined by portions of the inner laterally extending edge 107b, the inner laterally extending edge 109b, and the second longitudinal or left side edge 130 of the chassis 102. The outer laterally extending edges 107a, 109a may also define the front waist edge 121 and the laterally extending back waist edge 122 of the diaper pant 100P. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer substrate layer 162 and the inner substrate layer 164. The belt elastic material may include one or more elastic elements such as strands, ribbons, films, or panels extending along the lengths of the elastic belts. As shown in FIGS. 2, 3A, and 3B, the belt elastic material may include a plurality of elastic strands 168 which may be referred to herein as outer, waist elastics 170 and inner, waist elastics 172. Elastic strands 168, such as the outer waist elastics 170, may continuously extend laterally between the first and second opposing end regions 106a, 106b of the first elastic belt 106 and between the first and second opposing end regions 108a, 108b of the second elastic belt 108. In some embodiments, some elastic strands 168, such as the inner waist elastics 172, may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2. The belt elastic material may be joined to the outer and/or inner layers continuously or intermittently along the interface between the belt elastic material and the inner and/or outer belt layers.

In some configurations, the first elastic belt 106 and/or second elastic belt 108 may define curved contours. For example, the inner lateral edges 107b, 109b of the first and/or second elastic belts 106, 108 may include non-linear or curved portions in the first and second opposing end regions. Such curved contours may help define desired shapes to leg opening 112, such as for example, relatively rounded leg openings. In addition to having curved contours, the elastic belts 106, 108 may include elastic strands 168,

172 that extend along non-linear or curved paths that may correspond with the curved contours of the inner lateral edges 107b, 109b.

It is to be appreciated that the apparatuses and methods of assembly of elastic laminates and absorbent articles described herein and illustrated in the accompanying drawings are non-limiting example configurations. The features illustrated or described in connection with one non-limiting configuration may be combined with the features of other non-limiting configurations. Such modifications and variations are intended to be included within the scope of the present disclosure.

Figure 4A:
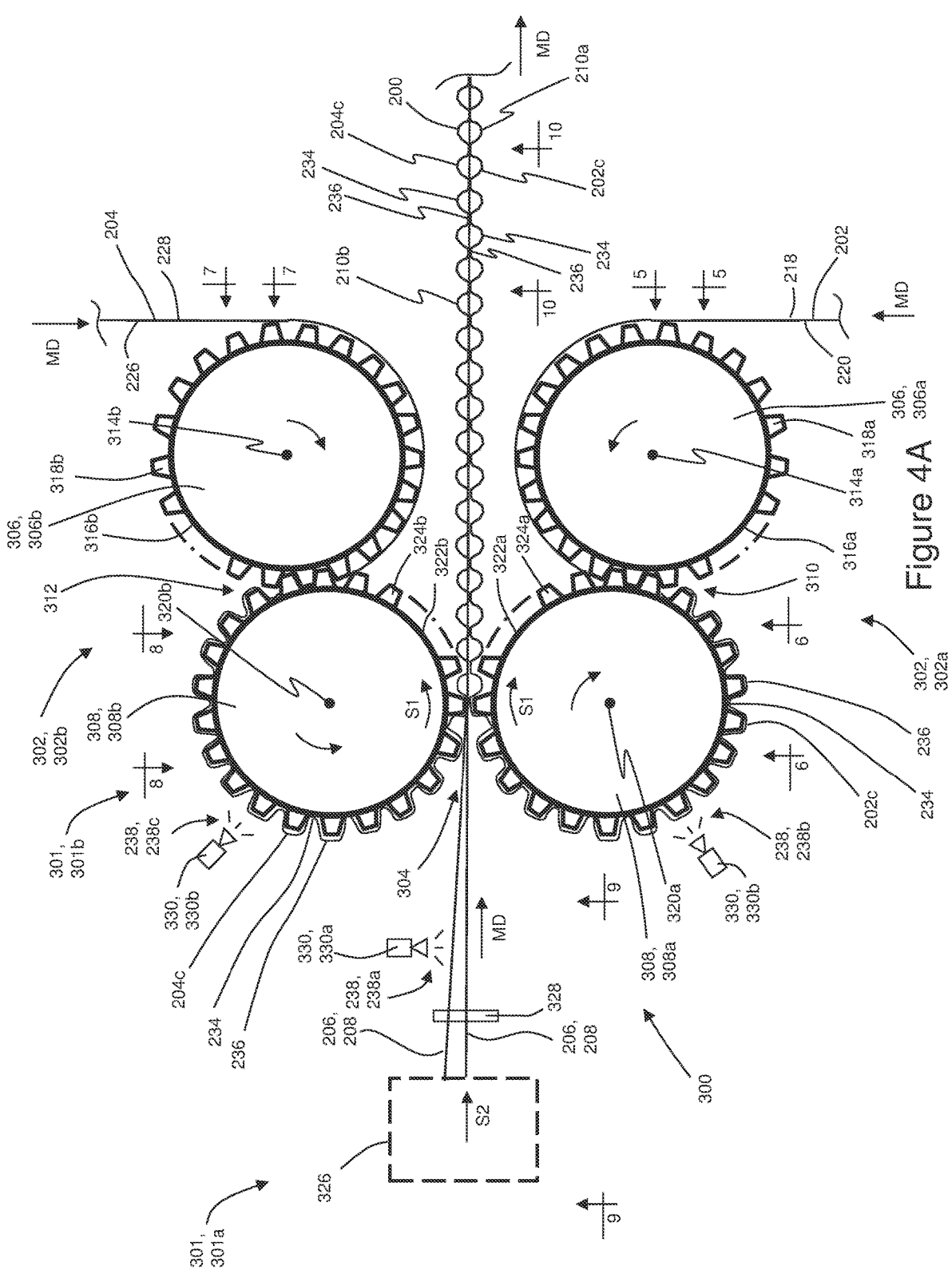
FIG. 4A is a schematic side view of a converting apparatus adapted to assemble a corrugated elastic laminate.
Figure 4B:
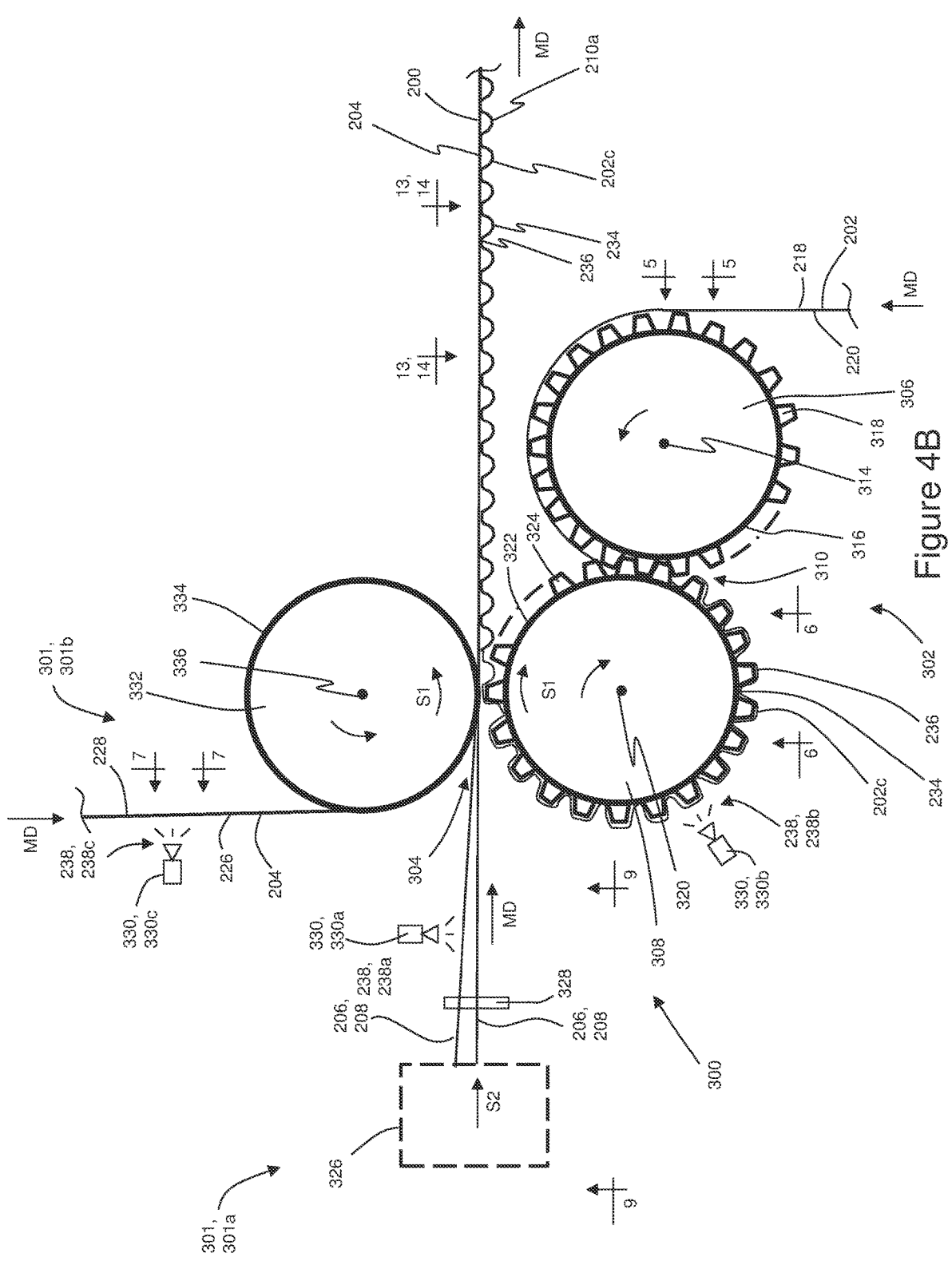
FIG. 4B is a schematic side view of another configuration of a converting apparatus adapted to manufacture a corrugated elastic laminate.
Figure 4C:
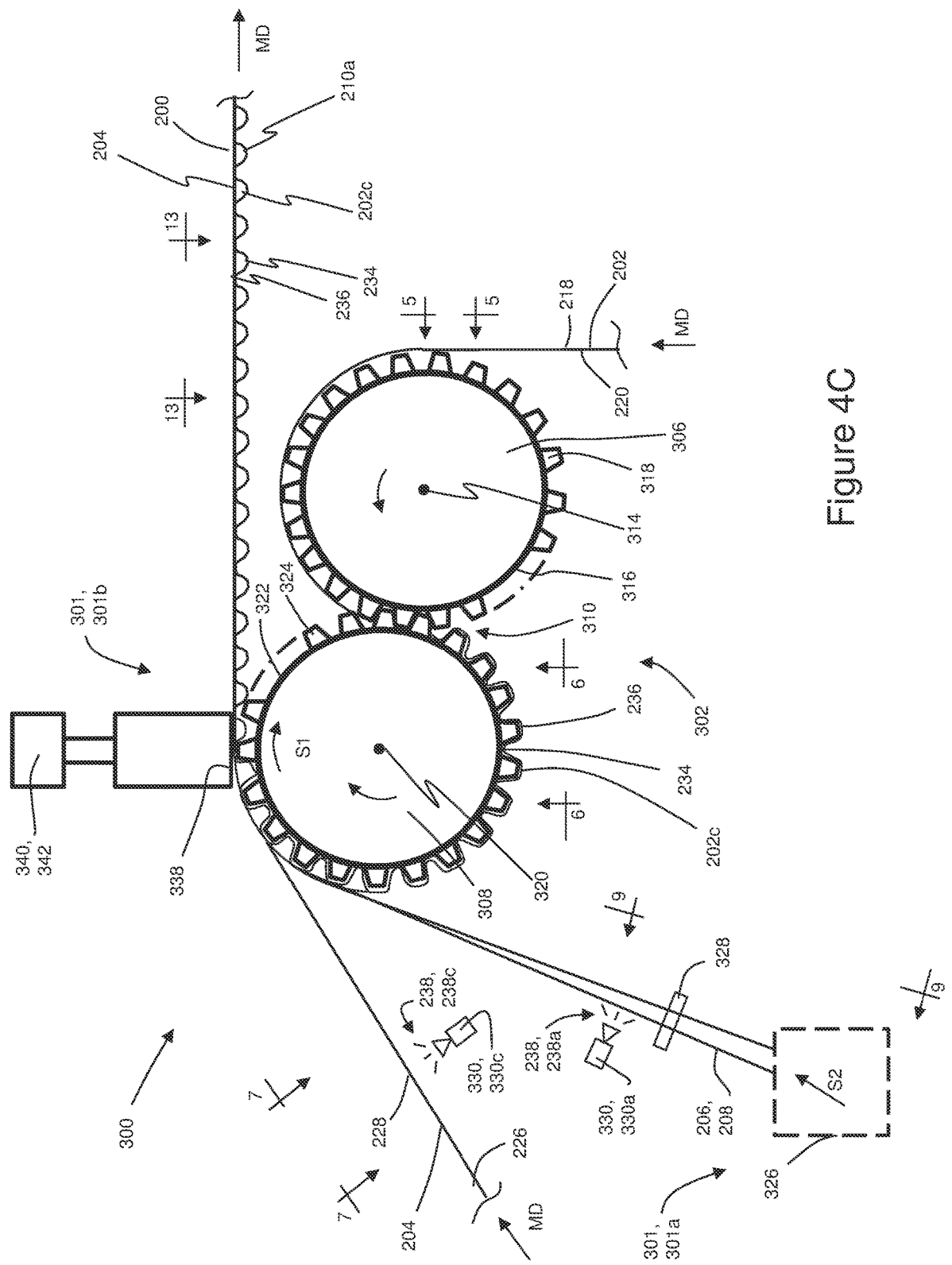
FIG. 4C is a schematic side view of another configuration of a converting apparatus adapted to manufacture a corrugated elastic laminate.

As previously mentioned, apparatuses and methods according to the present disclosure may be utilized to produce elastic laminates that may be used to construct various components of absorbent articles, such as elastic belts, leg cuffs, and the like. For example, FIGS. 4A-4C show schematic views of converting apparatuses 300 adapted to manufacture elastic laminates 200. As described in more detail below, the converting apparatuses 300 operate to advance a continuous length of a first substrate 202, a continuous length of a second substrate 204, and a continuous length of elastic material 206 along a machine direction MD. It is also to be appreciated that in some configurations, the first substrate 202 and second substrate 204 herein may be defined by two discrete single layer substrates or may be defined by multi-layered laminates. And in some configurations, the first substrate 202 and/or the second substrate 204 may comprise nonwovens. The apparatus 300 may include one or more corrugating devices 302 with corrugating rolls 306, 308 adapted to rotate about axes 314, 320. Each corrugating roll 306, 308 may include protrusions 318, 324 protruding outward from outer circumferential surfaces 316, 322. The protrusions 318, 324 are configured in a meshing relationship that form corrugations 210 in either or both the first substrate 202 and/or the second substrate 204. The apparatus may also stretch the elastic material 206 and join the stretched elastic material 206 with the first and second substrates 202, 204 to produce an elastomeric laminate 200. Although the elastic material 206 is illustrated and referred to herein as elastic strands 208, it is to be appreciated that elastic material 206 may include one or more continuous lengths of elastic strands, ribbons, and/or films.

As shown in FIG. 4A a converting apparatus 300 for producing an elastic laminate 200 may include a first corrugating device 302a and a second corrugating device 302b. During operation, the first corrugating device 302a corrugates the first substrate 202, and the second corrugating device 302b corrugates the second substrate 204. In turn, a first corrugated substrate 202c advances from the first corrugating device 302a through the combining nip 304, and a second corrugated substrate 204c advances from the second corrugating device 302b through the combining nip 304. In addition, elastic strands 208 also advance in the machine direction MD through the combining nip 304 between the first corrugated substrate 202c and the second corrugated substrate 204c to form the laminate 200. The elastic strands 208 may also be stretched in the machine direction MD before or while advancing the through the combining nip 304. As discussed in more detail below with reference to FIGS. 4A-16, discrete lengths of the elastic strands 208 are bonded with and between the first corrugated substrate 202c and the second corrugated substrate 204c with first bonds 230, and the first corrugated substrate 202c is bonded directly with the second corrugated substrate 204c with second bonds 232 positioned intermittently along the machine direction MD between the first bonds 230. As such, the elastic strands 208 may extend through the second bonds 232, and as the elastic laminate 200 is stretched and retracted, the elastic strands 208 may correspondingly retract and stretch through the second bonds 232.

The first corrugating device 302a may be positioned adjacent the second corrugating device to define a combining nip 304 therebetween. As shown in FIGS. 4A, 5, and 6, the first corrugating device 302a is configured to form first corrugations 210a in the first substrate 202, and the second corrugating device 302b is configured to form second corrugations 210b in the second substrate 204. As shown in FIGS. 4A, 5, and 6, the first substrate 202 comprises a first longitudinal edge 214 and a second longitudinal edge 216 separated from the first longitudinal edge 214 in the cross direction CD to define a width. The first substrate 202 also includes a first surface 218 and an opposing second surface 220. Similarly, as shown in FIGS. 4A, 7, and 8, the second substrate 204 comprises a first longitudinal edge 222 and a second longitudinal edge 224 separated from the first longitudinal edge 222 in the cross direction CD to define a width. The second substrate 204 also includes a first surface 226 and an opposing second surface 228.

As shown in FIG. 4A, the first corrugating device 302a may include a first corrugating roll 306a adjacent a second corrugating roll 308a to define a first corrugating nip 310 therebetween. The first corrugating roll 306a may be adapted to rotate about an axis 314a and include an outer circumferential surface 316a and protrusions 318a protruding radially outward. The second corrugating roll 308a may be adapted to rotate about an axis 320a in a direction opposite the first corrugating roll 306a. The second corrugating roll 308a may include an outer circumferential surface 322a and protrusions 324a protruding radially outward. The protrusions 318a of the first corrugating roll 306a are configured to be in a meshing relationship with the protrusions 324a of the second corrugating roll 308a at the first corrugating nip 310. The first substrate 202 may advance in the machine direction MD to the first corrugating device 302a with the second surface 220 of the first substrate 202 in a facing relationship with the outer circumferential surface 316a and protrusions 318a of the first corrugating roll 306a. As the first corrugating roll 306a rotates about the axis 314a, the first substrate 202 advances through the first corrugating nip 310 and between meshing portions of the protrusions 318a of the first corrugating roll 306a and the protrusions 324a of the second corrugating roll 308a. In turn, the first substrate 202 is corrugated by being generally conformed to the periphery of the second corrugating roll 308a to form corrugations 310a defined by ridges 234 that alternate with depressions 236 along the machine direction MD of a first corrugated substrate 202c. With continued reference to FIG. 4A, the first substrate 202 is corrugated and transferred onto the second corrugating roll 308a at the first corrugating nip 310. As such, the first substrate 202 is transferred onto the second corrugating roll 306a with the first surface 218 of the first substrate 202 in a facing relationship with the outer circumferential surface 322a and protrusions 324a of the second corrugating roll 308a. In turn, the first corrugated substrate 202c may advance on the outer circumferential surface 322a and protrusions 324a of the second corrugating roll 308a from the first corrugating nip 310 and through the combining nip 304.

With continued reference to FIG. 4A, the second corrugating device 302b may include a first corrugating roll 306b adjacent a second corrugating roll 308b to define a second corrugating nip 312 therebetween. The first corrugating roll 306b may be adapted to rotate about an axis 314b and include an outer circumferential surface 316b and protrusions 318b protruding radially outward. The second corrugating roll 308b may be adapted to rotate about an axis 320b in a direction opposite the first corrugating roll 306b. The second corrugating roll 308b may include an outer circumferential surface 322b and protrusions 324b protruding radially outward. The protrusions 318b of the first corrugating roll 306b are configured to be in a meshing relationship with the protrusions 324b of the second corrugating roll 308b at the second corrugating nip 312. The second substrate 204 may advance in the machine direction MD to the second corrugating device 302b with the first surface 226 of the second substrate 204 in a facing relationship with the outer circumferential surface 316b and protrusions 318b of the first corrugating roll 306b. As the first corrugating roll 306b rotates about the axis 314b, the second substrate 204 advances through the second corrugating nip 312 and between meshing portions of the protrusions 318b of the first corrugating roll 306b and the protrusions 324b of the second corrugating roll 308b. In turn, the second substrate 204 is corrugated by being generally conformed to the periphery of the second corrugating roll 308b to form corrugations 310b defined by ridges 234 that alternate with depressions 236 along the machine direction MD of a second corrugated substrate 204c. With continued reference to FIG. 4A, the second substrate 204 is corrugated and transferred onto the second corrugating roll 308b at the second corrugating nip 312. As such, the second substrate 204 is transferred onto the second corrugating roll 306b with the second surface 228 of the second substrate 204 in a facing relationship with the outer circumferential surface 322b and protrusions 324b of the second corrugating roll 308b. In turn, the second corrugated substrate 204c may advance on the outer circumferential surface 322b and protrusions 324b of the second corrugating roll 308b from the second corrugating nip 312 and through the combining nip 304.

It is to be appreciated that the corrugating devices 302 may include corrugating rolls 306, 308 that may be configured in various ways. For example, as shown in FIG. 4A1, the first corrugating roll 306 and/or second corrugating roll 308 may be configured in the form of gears 342 wherein the protrusions 318, 324 may be configured as gear teeth 344. As such, the gear teeth 344 of the first corrugating roll 306 and the gear teeth 344 of the second corrugating roll 308 may intermesh at the corrugating nips 310, 312 to form corrugations in the first and/or second substrates 202, 204, such as described above with reference to FIG. 4A. As shown in FIG. 4A1, the gear teeth 344 may also include outer radial surfaces 346. As such, outer radial surfaces 346 of the second corrugating rolls 308 may be in opposing relationships that press the first substrate 202, the second substrate 204, and the elastic strands 208 together at the combining nip 304, such as described above with reference to FIG. 4A. It is to be appreciated that FIG. 4A1 is a generic representation of a gear 342 and it is to be appreciated that the gears 342 herein may be configured with various different quantities and geometries of gear teeth such as described for example in PCT Patent Publication Nos. WO95/34264A1 and WO2020/230012A1, which are both incorporated herein by reference. It is also to be appreciated that the corrugating rolls 306, 308 may be constructed from various types of materials, such as for example, plastic, silicone, rubber, and/or various types of metals. In some configurations, some corrugating rolls 306, 308 may include a nonstick coating, such as a plasma coating for example. In some configurations, some corrugating rolls 306, 308 may operate with vacuum air pressure that may operate to force and/or hold the first and/or second substrates onto the corrugating rolls 306, 308. Such vacuum air pressure may also help fix the formation of corrugations in the first and/or second substrates 202, 204 by maintaining conformance of the first and/or second substrates 202, 204 with the shapes of the corrugating rolls 306, 308.

It is also to be appreciated that the gear teeth 344 of meshing corrugating rolls 306, 308 may be configured to preserve a gap clearance large enough for the substrates to advance between without being compressed. In some configurations, the tooth geometry may be modified to create a gap clearance between the gear teeth and/or the drive may be modified to maintain the clearance, i.e., no rolling contact. In some configurations, each corrugating roll may include a drive gear to drive and maintain the clearance between the intermeshing corrugating rolls.

Figure 9:
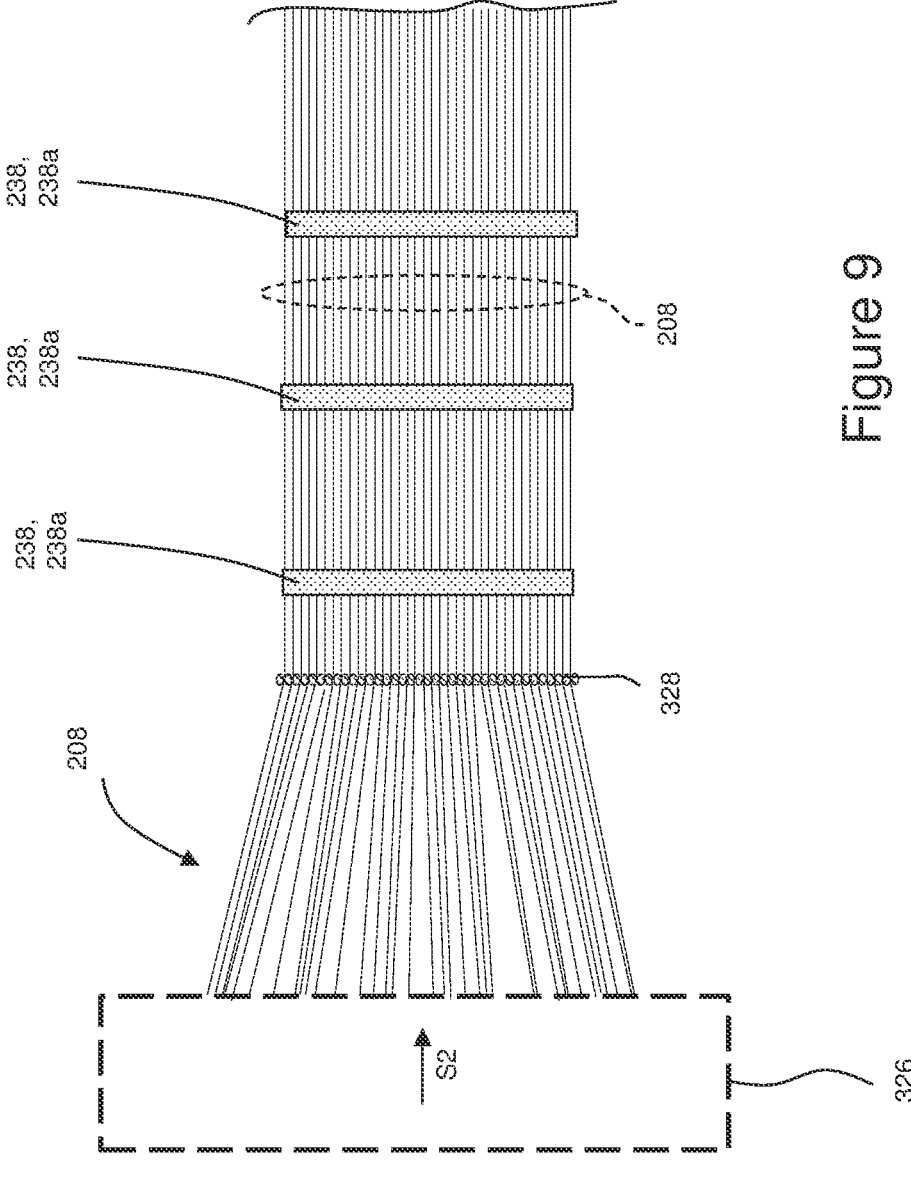
FIG. 9 is a view of elastics strands taken along section 9-9 in FIGS. 4A, 4B, and 4C.

As previously mentioned, advancing elastic strands 208 may be bonded between the first corrugated substrate 202c and the second corrugated substrate 204c at the combining nip 304. As shown in FIGS. 4A and 9, the converting apparatus 300 may include an elastic strand supply apparatus 326, such as one or more unwinders generically represented by a dash line rectangle, that may include one or more spools of elastic strands 208. During operation, the elastic strands 208 advance in the machine direction MD from the unwinder 326 to the combining nip 304. In addition, the elastic strands 208 may be stretched along the machine direction MD while advancing between the unwinder 326 and the combining nip 304. The stretched elastic strands 208 are also joined with the first corrugated substrate 202c and the second corrugated substrate 204c at the combining nip 304 to produce an elastomeric laminate 200. It is to be appreciated that the elastic strands 208 may advance along and/or around one or more guide rollers. It is also to be appreciated that the elastic strands 208 may be stretched along a continuous path while advancing in the machine direction MD or may be stretched in various steps that provide multiple increases in elongation while advancing in the machine direction MD.

In some configurations, components of the converting apparatus may be characterized as metering devices 301 that are adapted to advance and stretch the elastic strands 208 in the machine direction. As such, the elastic strands may advance from a first metering device 301a at a first speed to a second metering device 301b at a second speed, wherein the second speed is greater than the first speed. For example, the unwinder 326 may be characterized as a first metering device 301a, and the combing nip 304 defined between the first and second corrugating devices 302a, 302b may be characterized as a second metering device 301b. As shown in FIG. 4A, the second corrugating roll 308a of the first corrugating device 302a may rotate such that the protrusions 324a have surface speeds S1, and the second corrugating roll 308b of the second corrugating device 302b may rotate such that the protrusions 324b have the same, or substantially the same, surface speed S1. As such, the first corrugated substrate 202c and the second corrugated substrate 204c may advance at speeds S1 through the combining nip 304. It is to be appreciated that the first and/or second corrugated substrates 202c, 204c may advance at various speeds S1. In some configurations, the first corrugated substrate 202c and/or the second corrugated substrate 204c may advance at speed S1 from about 150 meters/minute to about 500 meters/minute, specifically reciting all 1 meter/minute increments within the above-recited range and all ranges formed therein or thereby.

In some configurations, the elastic strands 208 may also be stretched in the machine direction MD and combined with the first corrugated substrate 202c and the second corrugated substrate 204c in the stretched state. For example, with continued reference to FIGS. 4A and 9, the unwinder 326 may unwind or otherwise supply the elastic strands 208 advancing at a speed S2 in the machine direction MD to the combining nip 304. In some configurations, the speed S2 is less than the speed S1, and as such, the elastic strands 208 are stretched in the machine direction MD. In turn, the stretched elastic strands 208 advance through the combining nip 328 and bonded between the first and second corrugated substrates 202c, 204c to produce a continuous length of elastomeric laminate 200.

As previously mentioned, the apparatus 301 may include an elastic strand supply apparatus 326, such as one or more unwinders, that supplies a plurality of elastic strands 208. It is to be appreciated the unwinders 326 herein may be configured in various ways. For example, the unwinder 326 may be configured with individual spools with mandrel and/or surface driven unwinders, overend unwinders, and/or beam unwinders (also referred to as warp beams). Various types of unwinders are disclosed in U.S. Pat. Nos. 6,676, 054; 7,878,447; 7,905,446; 9,156,648; 4,525,905; 5,060, 881; and 5,775,380; U.S. patent application Ser. No. 17/189, 476, filed on Mar. 2, 2021; and U.S. Patent Publication Nos. 2004/0219854 A1; 2018/0168879 A1; and 2018/0170026 A1, all of which are incorporated by reference herein. Additional examples of elastics and associated handling equipment are available from Karl Mayer Corporation. It is to be appreciated that the converting apparatus 300 may be configured to assemble elastomeric laminates 200 with elastic strands 208 unwound from more than one unwinder 326 in combination with elastic strands supplied from the same and/or different types of elastic unwinder configurations. It is also to be appreciated that the elastic strands 208 may include various types of spin finish, also referred herein as yarn finish, configured as coating on the elastic strands 208 that may be intended to help prevent the elastic strands from adhering to themselves, each other, and/or downstream handling equipment. As such, the apparatus may also be configured to remove or partially remove the spin finish from the elastic strands, such as disclosed for example in U.S. Patent Publication No. 2018/0168877 A1, which is incorporated by reference herein.

It is also to be appreciated that the converting apparatus 300 may include one or more unwinders 326 that may supply various quantities of elastic strands 208. In some configurations, the unwinders 302 herein may include from 1 to about 3000 spools positioned thereon, and thus, may have from 1 to about 3000 elastic strands 208 advancing therefrom, specifically reciting all 1 spool and strand increments within the above-recited range and all ranges formed therein or thereby. In turn, the elastomeric laminates 200 herein may include from 1 to about 3000 elastic strands 208 spaced apart from each other in the cross direction CD, specifically reciting all 1 elastic strand increments within the above-recited range and all ranges formed therein or thereby.

It is also to be appreciated that the apparatuses and processes may be configured such that elastic strands 208 may be advanced from the unwinders 326 and directly to the assembly process without having to touch additional machine components, such as for example, guide rollers. It is also to be appreciated that in some configurations, elastic strands 208 may be advanced from the unwinders 326 and may be redirected and/or otherwise touched by and/or redirected by machine components, such as for example guide rollers, before advancing to the assembly process.

As shown in FIGS. 4A and 9, the elastic strands 208 may also advance through a strand guide 328 before being combined with the first substrate 204 and the second substrate 206. The strand guide 328 may space or separate neighboring elastic strands 208 from each other at a desired distance in a cross direction CD before being combined with the first substrate 204 and the second substrate 206. As shown in FIGS. 4A and 9, the elastic strands 208 may advance through a strand guide 328 positioned between the unwinder 326 and the nip 304. The strand guide 328 may operate to change and/or dictate and/or fix the cross directional CD separation distance between neighboring elastic strands 208 advancing into the nip 304 and in the assembled elastomeric laminate 200. It is to be appreciated that the elastic strands 208 may be separated from each other by various distances in the cross direction CD advancing into the nip 304 and in the assembled elastomeric laminate 200. In some configurations, neighboring elastic strands 208 may be separated from each other by about 0.5 mm to about 4 mm in the cross direction CD, specifically reciting all 0.1 mm increments within the above-recited range and all ranges formed therein or thereby. It is to be appreciated that the strand guide 328 may be configured in various ways. In some configurations, the strand guide 328 may be configured as a comb that may comprise a plurality of tines or reeds. In turn, the advancing elastic strands 208 are separated and spaced apart from each other by the tines or reeds in the cross direction CD from each other. In some configurations, the strand guide 328 may include a plurality of rollers that separate and space the elastic strands in the cross direction CD from each other.

It is to be appreciated that different components may be used to construct the elastomeric laminates 200 in accordance with the methods and apparatuses herein. For example, the first and/or second substrates 204, 206 may include nonwovens and/or films. In addition, the elastic strands 208 may be configured in various ways and may have various decitex values. In some configurations, the elastic strands 208 may be configured with decitex values ranging from about decitex to about 1000 decitex, specifically reciting all 1 decitex increments within the above-recited range and all ranges formed therein or thereby.

Referring again FIG. 4A, the converting apparatus 300 may include one or more adhesive applicator devices 330 that may apply adhesive 238 to the elastic strands 208, the first substrate 202, and/or the second substrate 204 before being combined to form the elastomeric laminate 200. It is to be appreciated that the adhesive applicator devices 300 herein be configured in various ways, such as for example, spray nozzles, strand coating, and/or slot coating devices. In some configurations, the adhesive applicator devices 330 may be configured in accordance with the apparatuses and/or methods disclosed in U.S. Pat. Nos. 8,186,296; 9,265,672; 9,248,054; and 9,295,590 and U.S. Patent Publication No. 2014/0148773 A1, all of which are incorporated by reference herein.

Figure 10:
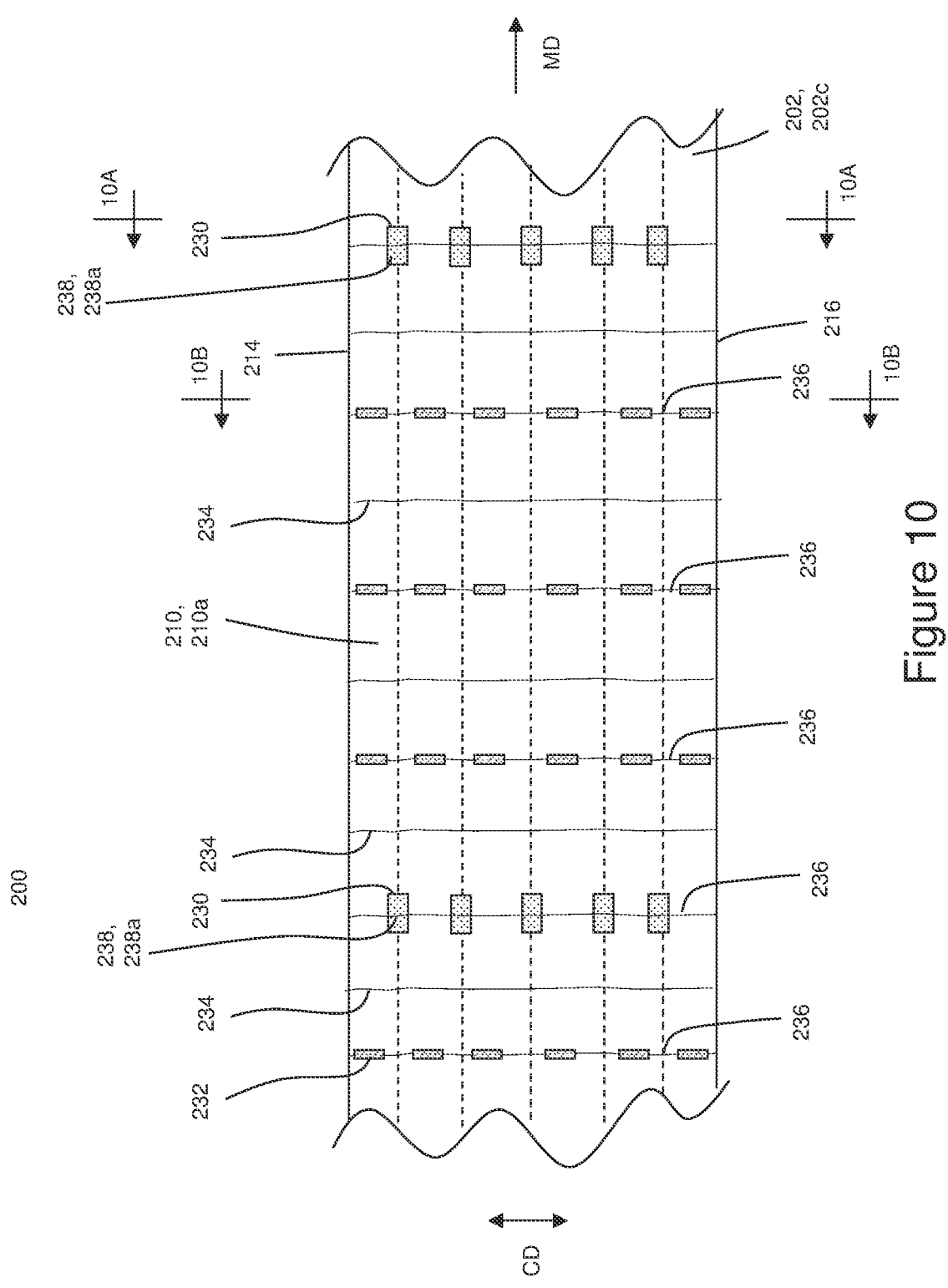
FIG. 10 is a view of an elastic laminate taken along section 10-10 in FIG. 4A.
Figure 10A:
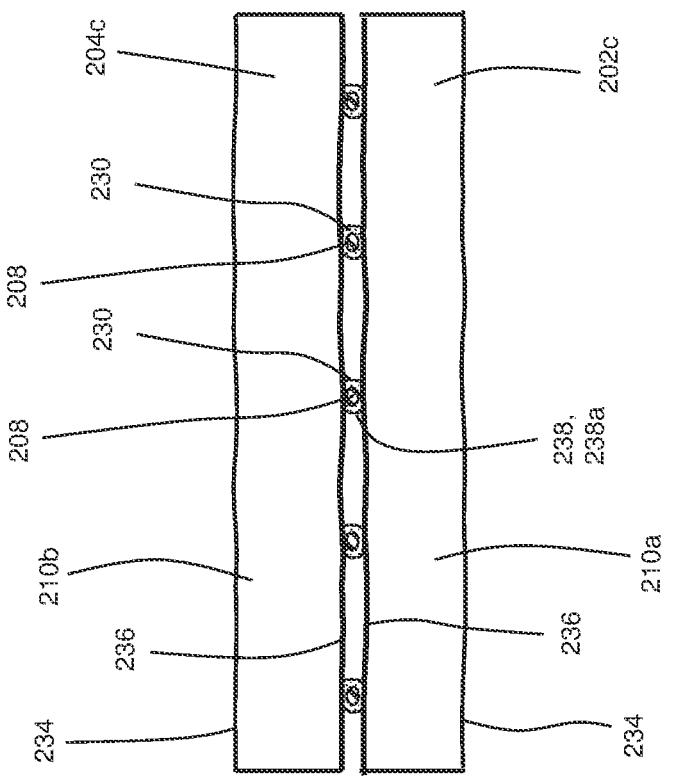
FIG. 10A is a view of the elastic laminate taken along section 10A-10A in FIG. 10.
Figure 11:
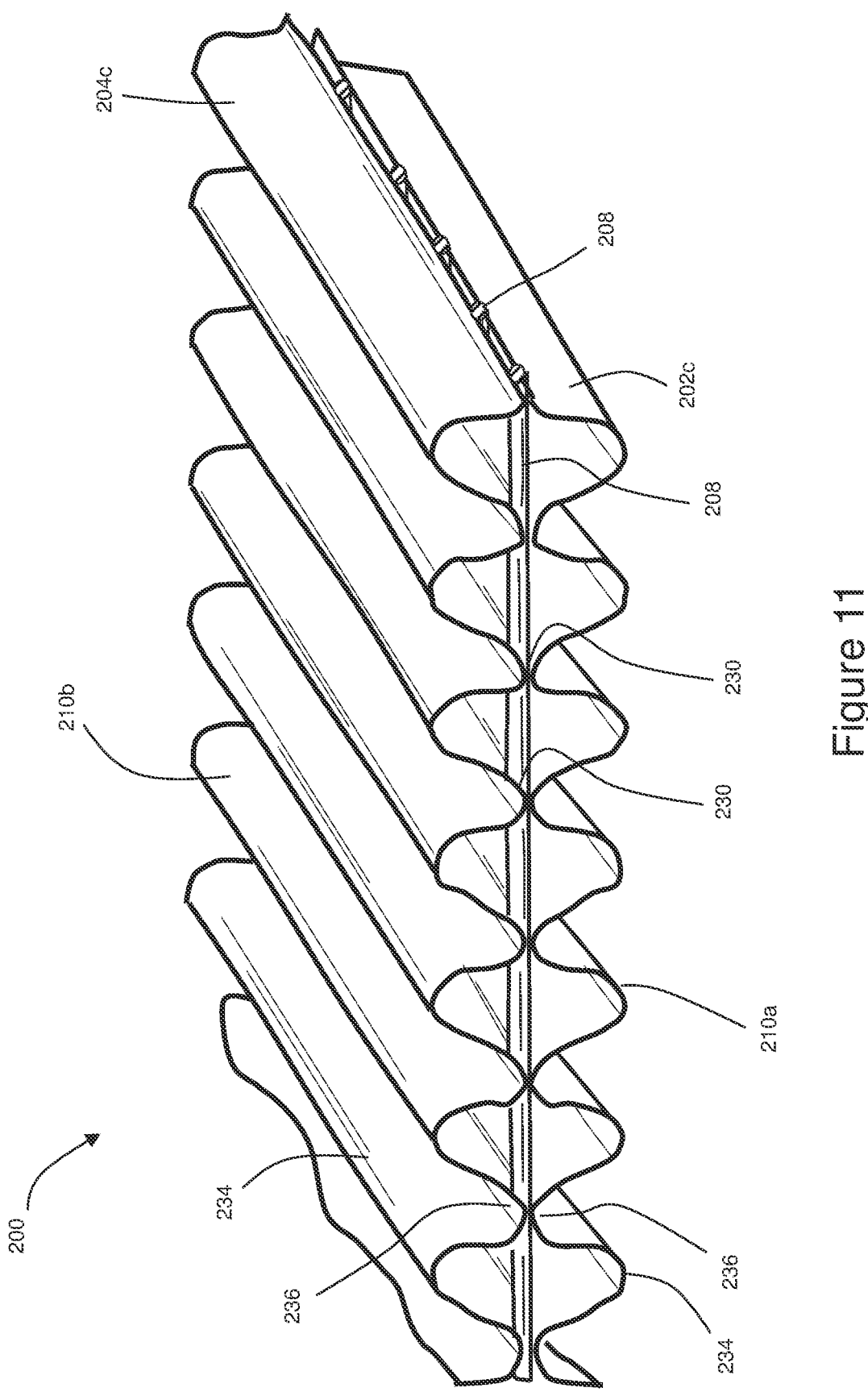
FIG. 11 is a perspective view of the elastic laminate of FIG. 10.

As shown in FIGS. 4A and 9, a first adhesive applicator device 330a may be adapted to apply a first adhesive 238a to the advancing elastic strands 208, and the elastic strands 208 may be in a stretched state when the first adhesive 238a is applied. The first adhesive applicator device 330a may operate to apply the first adhesive 238a intermittently to discrete lengths of the elastic strands 208 along the machine direction MD before the elastic strands 208 advance to the combining nip 304. FIGS. 10 and 11 show views of the elastic laminate 200 advancing from the combining nip 304. For purposes of clarity, FIGS. 10 and 11 illustrate five elastic strands 208 in the elastic laminate 200, however, it is to be appreciated that the elastic laminate 200 may include more or less than five elastic strands 208, as discussed above. As shown in FIGS. 10 and 10A, the first adhesive 238a forms the first bonds 230 in the elastic laminate 200 that bond the first corrugated substrate 202c, the second corrugated substrate 204c, and the elastic strands 208 together. In particular, the first bonds 230 are intermittently spaced along the machine direction MD and bond discrete lengths of the stretched elastic strands 208 with the first corrugated substrate 202c and the second corrugated substrate 204c.

As shown in FIG. 4A, the converting apparatus 300 may also include a second adhesive applicator device 330b and/or a third adhesive applicator device 330c. The second adhesive applicator device 330b may be adapted to apply a second adhesive 238b to the first substrate 202. For example, the second adhesive applicator device 330b may operate to apply the second adhesive 238b intermittently to the first corrugated substrate 202c advancing on the second corrugating roll 308a. In some configurations, the second adhesive applicator device 330b may apply the second adhesive 238b to the depressions 236 of the first corrugated substrate 202c without applying the second adhesive 238b to the ridges 234 of the first corrugated substrate 202c. The third adhesive applicator device 330c may be adapted to apply a third adhesive 238c to the second substrate 204. For example, the third adhesive applicator device 330c may operate to apply the third adhesive 238c intermittently to the second corrugated substrate 204c advancing on the second corrugating roll 308b. In some configurations, the third adhesive applicator device 330c may apply the third adhesive 238c to the depressions 236 of the second corrugated substrate 204c without applying the third adhesive 238c to the ridges 234 of the second corrugated substrate 204c.

Figure 10B:
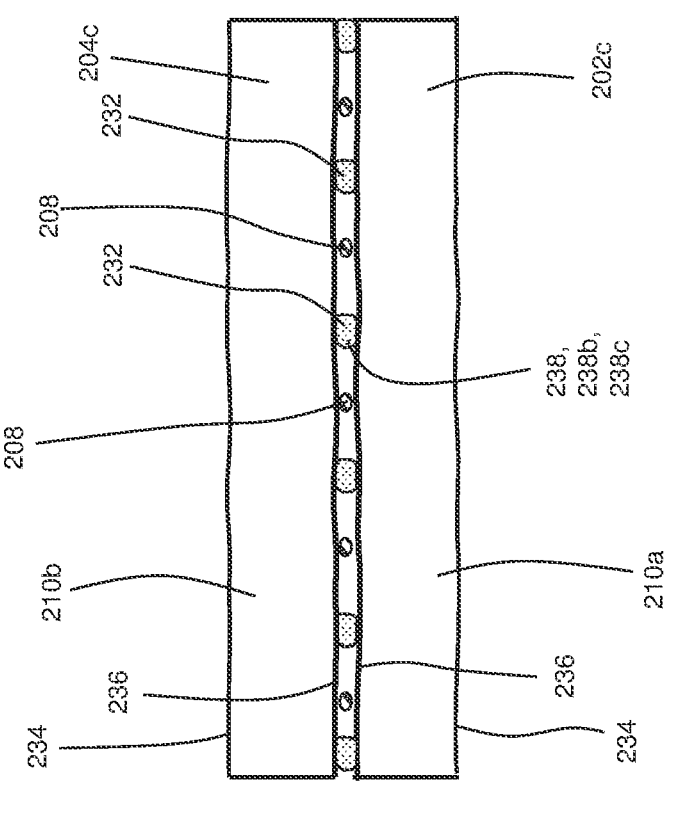
FIG. 10B is a view of the elastic laminate taken along section 10B-10B in FIG. 10.
Figure 12:
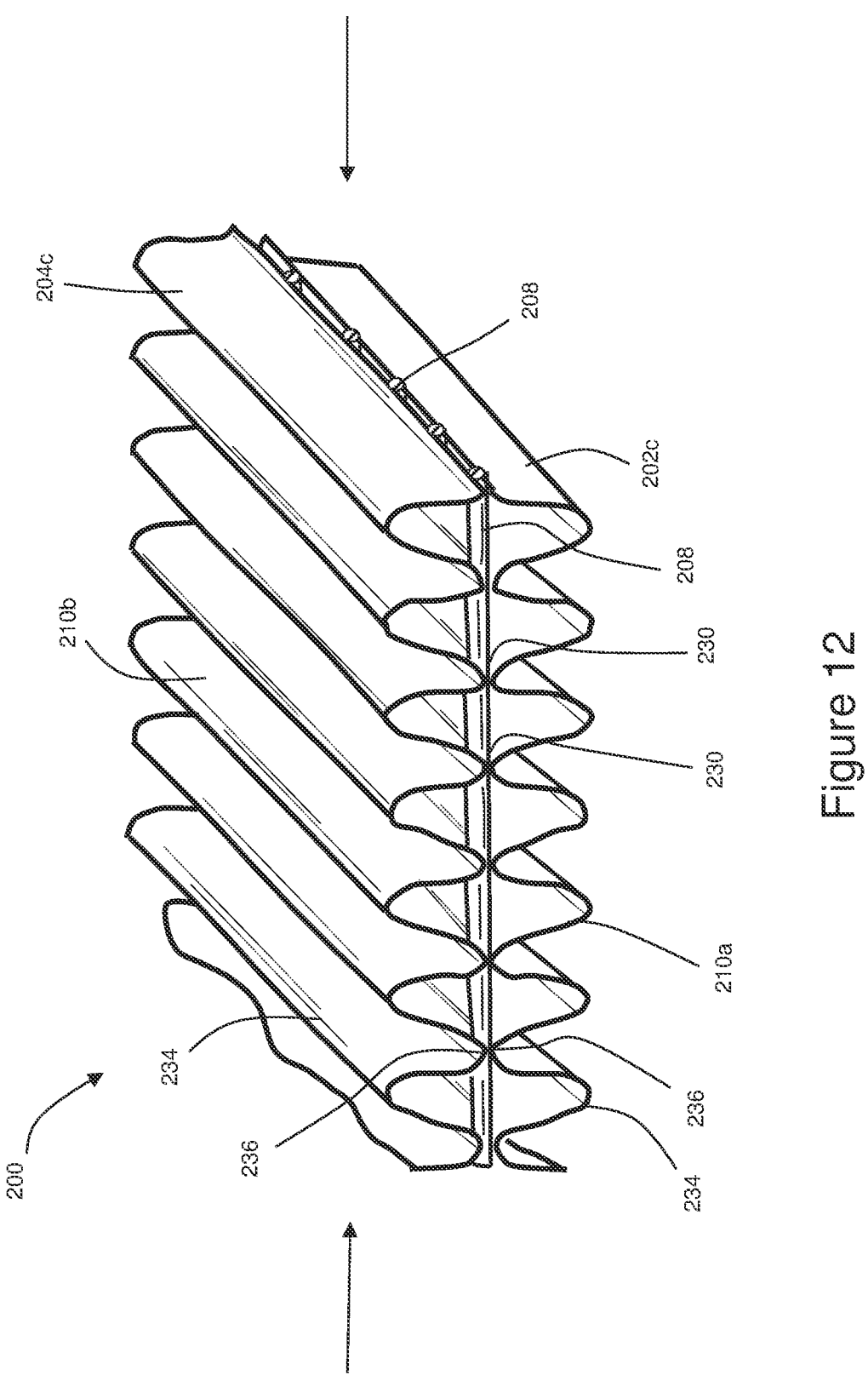
FIG. 12 is a perspective view of the elastic laminate of FIG. 11 in a contracted state.

As shown in FIGS. 10 and 10B, the second adhesive 238b and/or the third adhesive 238c may form the second bonds 232 in the elastic laminate 200 that bond the first corrugated substrate 202c with the second corrugated substrate 204c. In particular, the second bonds 232 may be intermittently spaced along the machine direction MD and bond the depressions 236 of the first corrugated substrate 202c together with the depressions 236 of the second corrugated substrate 204c. The second bonds 232 may also be intermittently spaced along the cross direction CD. The elastic strands 208 may extend through and between the second bonds 232. Thus, as the elastic laminate 200 is stretched and retracted, the elastic strands 208 may correspondingly retract and stretch without being significantly inhibited by the second bonds 232. In contrast to the second bonds 232, discrete lengths of elastic strands 208 are anchored with the first corrugated substrate 202c and the second corrugated substrate 204c by the first bonds 230. As such, the anchored discrete lengths of elastic strands 208 will move along with the portions of the first corrugated substrate 202c and the second corrugated substrate 204c bonded with the first bonds 230 as the elastic laminate 200 is stretched and retracted, as shown in FIGS. 11 and 12. It is to be appreciated that the first adhesive 238a, the second adhesive 238b, and/or the third adhesive 238c may be the same adhesives or different adhesives. In addition, the first adhesive 238a, the second adhesive 238b, and/or the third adhesive 238c may be applied with the same basis weights or different basis weights. For example, the first adhesive 238a may be applied with a first basis weight, the second adhesive 238b may be applied with a second basis weight, and/or the third adhesive 238c may be applied with a third basis weight. In some configurations, the second basis weight and/or the basis weight may be less than the first basis weight.

It is also to be appreciated that the second bonds 232 may be adhesive bonds and/or mechanical bonds. For example, the converting apparatus 300 shown in FIG. 4A may be configured to mechanically bond the first corrugated substrate 202c with the second corrugated substrate 204c to form the second bonds 232. In some configurations, the second corrugating rolls 308 of the first corrugating device 302a and the second corrugating roll 308b of the second corrugating device may be configured to operate as a mechanical bonding device. For example, as shown in FIG. 4A2, the second corrugating roll 308 of the first corrugating device 302a and/or the second corrugating roll 308b may include bonding elements 348 positioned on the protrusions 324 or gear teeth 344. For example, bonding elements 348 may extend radially outward from the outer radial surfaces 346 of gear teeth 344 to define pressing surfaces 350. As the second corrugating rolls 308a, 308b rotate, the elastic laminate 200 is advanced between the pressing surfaces 350 of one corrugating roll 308 and the outer radial surfaces 346 of an opposing corrugating roll 308 at the combining nip 304. As such, the pressure created the interaction between the pressing surfaces 350 and the outer radial surfaces 346 operates to mechanically bond or weld the first corrugated substrate 202c and the second corrugated substrate 204c together to create the second bonds 232 between the depressions 234 of the first corrugated substrate 202c and the depressions 234 of the second corrugated substrate 204c. Heat and/or pressure between the pressing surfaces 350 of the protrusions 324a, 324b of the second corrugating rolls 308a, 308b may melt and bond the first and second corrugated substrates 202c, 204c together in areas supported by the pressing surfaces 350 of the protrusions 324a, 324b on the second corrugating rolls 308a, 308b. As such, the second bonds 232 may have shapes that correspond with and may mirror shapes of the pressing surfaces 350. In some configurations, the second corrugating roll 308a of the first corrugating device 302a and/or the second corrugating roll 308b of the second corrugating device 302b may also be heated. It is also to be appreciated that the second corrugating rolls 308a, 308b and/or protrusions 324a, 324b may be configured to apply heat and pressure in various ways to perform mechanical bonding, such as for example, the mechanical bonding devices and methods disclosed in in U.S. Pat. Nos. 4,854,984; 6,248,195; 8,778,127; 9,005,392; 9,962,297; and all of which are incorporated by reference herein. It is also to be appreciated that FIG. 4A2 is a generic representation of a gear 342, bonding elements 348, and pressing surfaces 350, and it is to be appreciated that such a gear 342 may be constructed from various materials and may be configured with various different quantities and geometries of gear teeth 344, bonding elements 348, and pressing surfaces 350, such as discussed above with reference to FIG. 4A1.

In some configurations, the converting apparatuses 300 herein may be configured to assemble elastic laminates 200 by combining a corrugated substrate and a substrate that has not been corrugated. For example, FIG. 4B shows a converting apparatus 300 with a corrugating device 302 including a first corrugating roll 306 and a second corrugating roll 308 configured similar to the first corrugating device 302a and associated first and second corrugating rolls 306a, 608a described above with reference to FIG. 4A. However, the converting apparatus of FIG. 4B does not include a second corrugating device 302b. Instead, the corrugating device 302 may be positioned adjacent an anvil roll 332 to define a combining nip 304 therebetween. As shown in FIGS. 4B and 4B1, the anvil roll 332 may include an outer circumferential surface 334 and is adapted to rotate about an axis 336.

As shown in FIG. 4B, the corrugating device 302 may include a first corrugating roll 306 adjacent a second corrugating roll 308 to define a corrugating nip 310 therebetween. The first corrugating roll 306 may be adapted to rotate about an axis 314 and include an outer circumferential surface 316 and protrusions 318 protruding radially outward. The second corrugating roll 308 may be adapted to rotate about an axis 320 in a direction opposite the first corrugating roll 306. The second corrugating roll 308 may include an outer circumferential surface 322 and protrusions 324 protruding radially outward. The protrusions 318 of the first corrugating roll 306 are configured to be in a meshing relationship with the protrusions 324 of the second corrugating roll 308 at the corrugating nip 310. The first substrate 202 may advance in the machine direction MD to the corrugating device 302 with the second surface 220 of the first substrate 202 in a facing relationship with the outer circumferential surface 316 and protrusions 318 of the first corrugating roll 306. As the first corrugating roll 306 rotates about the axis 314, the first substrate 202 advances through the corrugating nip 310 and between meshing portions of the protrusions 318 of the first corrugating roll 306 and the protrusions 324 of the second corrugating roll 308. In turn, the first substrate 202 is corrugated by being generally conformed to the periphery of the second corrugating roll 308 to form corrugations 310a defined by ridges 234 that alternate with depressions 236 along the machine direction MD of a first corrugated substrate 202c. With continued reference to FIG. 4B, the first substrate 202 is corrugated and transferred onto the second corrugating roll 308 at the corrugating nip 310. As such, the first substrate 202 is transferred onto the second corrugating roll 306 with the first surface 218 of the first substrate 202 in a facing relationship with the outer circumferential surface 322 and protrusions 324 of the second corrugating roll 308. In turn, the first corrugated substrate 202c may advance on the outer circumferential surface 322 and protrusions 324 of the second corrugating roll 308 from the corrugating nip 310 and through the combining nip 304.

The second substrate 204 may advance in the machine direction MD to the anvil roll 332 with the second surface 228 of the second substrate 204 in a facing relationship with the outer circumferential surface 334 of the anvil roll 332. As the anvil roll 332 rotates about the axis 336, the second substrate 204 advances on the outer circumferential surface 334 and through the combining nip 304. As such, the second substrate 204 is not corrugated before being combined with the first corrugated substrate 202c and elastic strands 208 at the combining nip 304.

As shown in FIG. 4B, advancing elastic strands 208 may be bonded between the first corrugated substrate 202c and the second substrate 204 at the combining nip 304. The elastic strands 208 may be configured to advance from an elastic strand supply apparatus 326, such as described above with reference to FIGS. 4A and 9. As such, the elastic strands 208 in FIG. 4B may advance in the machine direction MD from the unwinder 326 to the combining nip 304. In addition, the elastic strands 208 may be stretched along the machine direction MD while advancing between the unwinder 326 and the combining nip 304 as discussed above. The stretched elastic strands 208 are also joined with the first corrugated substrate 202c and the second substrate 204 at the combining nip 304 to produce the elastomeric laminate 200.

As discussed above, components of the converting apparatus may be characterized as metering devices 301 that are adapted to advance and stretch the elastic strands 208 in the machine direction, wherein the elastic strands may advance from a first metering device 301a at a first speed to a second metering device 301b at a second speed, wherein the second speed is greater than the first speed. With reference to FIG. 4B, the unwinder 326 may be characterized as a first metering device 301a and the combing nip 304 defined between the corrugating device 302 and the anvil roll 332 may be characterized as a second metering device 301b. As shown in FIG. 4B, the second corrugating roll 308 of the corrugating device 302 may rotate such that the protrusions 324a have surface speeds S1, and the anvil roll 332 may rotate such that the outer circumferential surface 334 has the same, or substantially the same, surface speed S1. As such, the first corrugated substrate 202c and the second substrate 204 may advance at speeds S1 through the combining nip 304. It is to be appreciated that the first corrugated substrate 202c and/or second substrate 204 may advance at various speeds S1. In some configurations, the first corrugated substrate 202c and/or the second substrate 204 may advance at speed S1 from about 150 meters/minute to about 500 meters/minute, specifically reciting all 1 meter/minute increments within the above-recited range and all ranges formed therein or thereby.

As discussed above, the elastic strands 208 may also be stretched in the machine direction MD and combined with the first corrugated substrate 202c and the second substrate 204 in the stretched state. For example, with continued reference to FIGS. 4B and 9, the unwinder 326 may unwind or otherwise supply the elastic strands 208 advancing at a speed S2 in the machine direction MD to the combining nip 304. In some configurations, the speed S2 is less than the speed S1, and as such, the elastic strands 208 are stretched in the machine direction MD. In turn, the stretched elastic strands 208 advance through the combining nip 328 and bonded between the first corrugated substrate 202c and the second substrates 204 to produce a continuous length of elastomeric laminate 200.

Referring again FIG. 4B, the converting apparatus 300 may include one or more adhesive applicator devices 330 that may apply adhesive 238 to the elastic strands 208 the first substrate 202, and/or the second substrate 204 before being combined to form the elastomeric laminate 200. As discussed above, the adhesive applicator devices herein 330 be configured in various ways, such as for example, spray nozzles, strand coating, and/or slot coating devices. In some configurations, the adhesive applicator devices 330 may be configured in accordance with the apparatuses and/or methods disclosed in U.S. Pat. Nos. 8,186,296; 9,265,672; 9,248,054; and 9,295,590 and U.S. Patent Publication No. 2014/0148773 A1, all of which are incorporated by reference herein.

Figure 13:
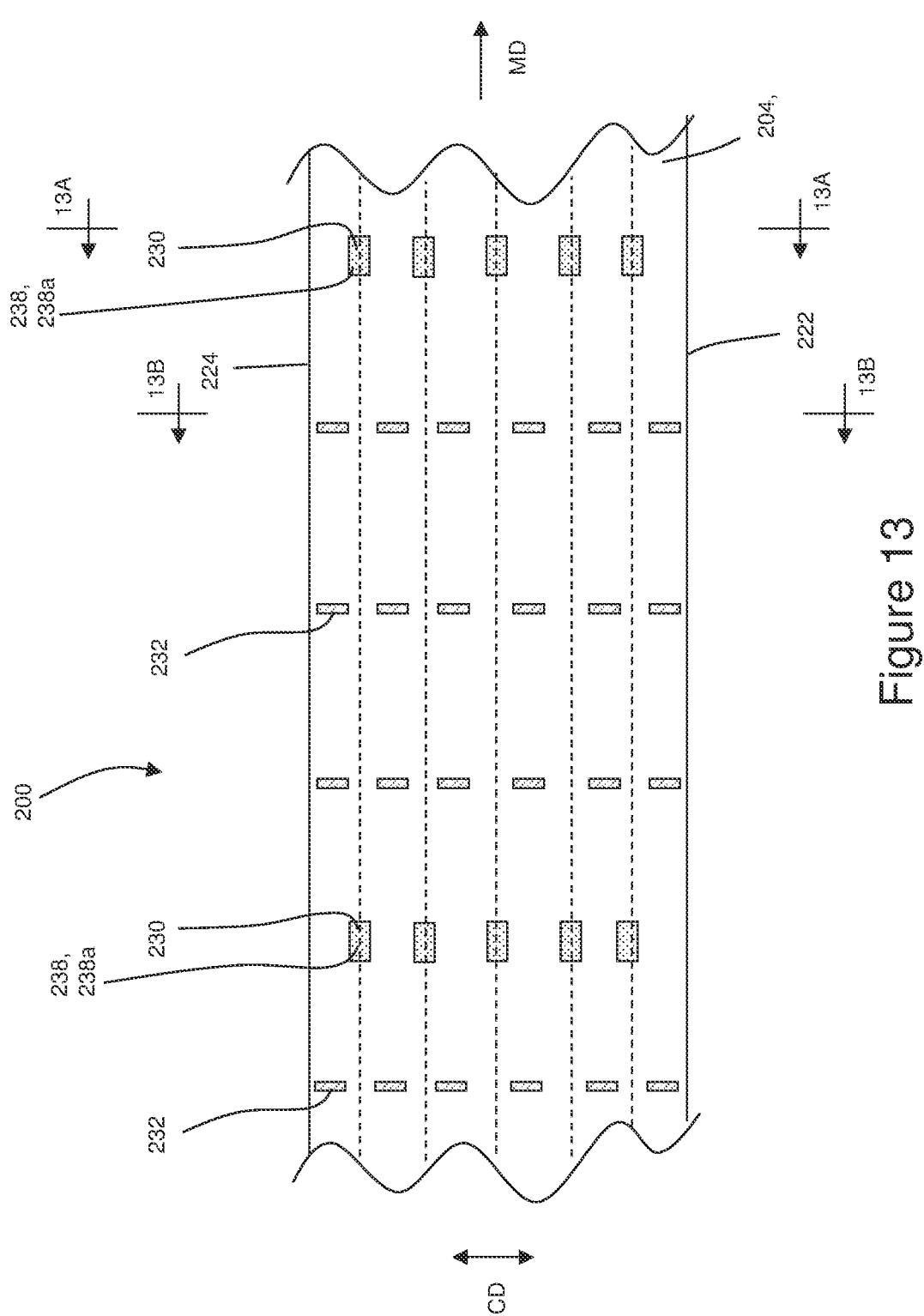
FIG. 13 is a view of an elastic laminate taken along section 13-13 in FIGS. 4B and 4C.
Figure 15:
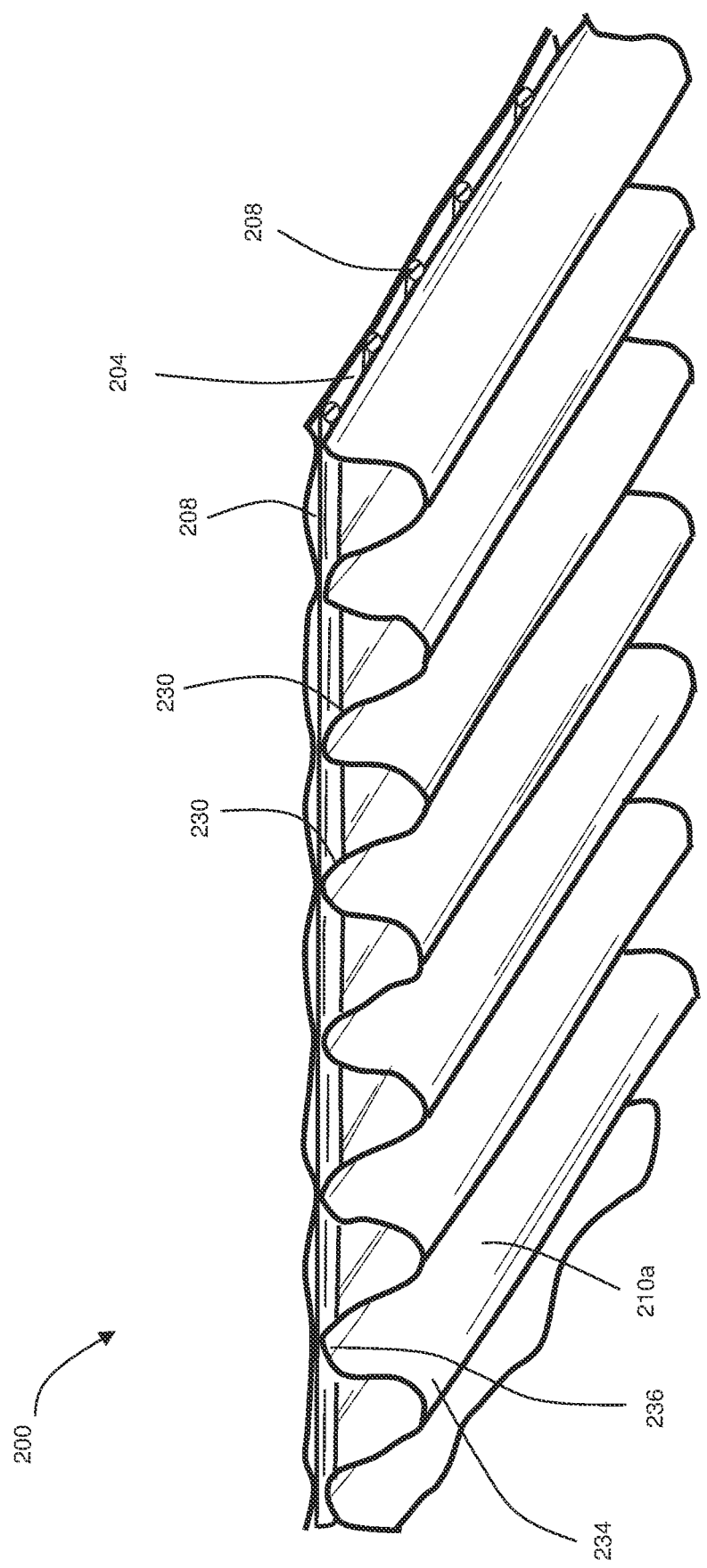
FIG. 15 is a perspective view of the elastic laminate of FIGS. 13 and 14.

As shown in FIGS. 4B and 9, a first adhesive applicator device 330a may be adapted to apply a first adhesive 238a to the advancing elastic strands 208, and the elastic strands 208 may be in a stretched state when the first adhesive 238a is applied. The first adhesive applicator device 330a may operate to apply the first adhesive 238a intermittently to discrete lengths of the elastic strands 208 along the machine direction MD before the elastic strands 208 advance to the combining nip 304. FIGS. 13 and 15 show views of the elastic laminate 200 advancing from the combining nip 304.

For purposes of clarity, FIGS. 13 and 15 illustrate five elastic strands 208 in the elastic laminate 200, however, it is to be appreciated that the elastic laminate 200 may include more or less than five elastic strands 208, as discussed above. As shown in FIGS. 13 and 13A, the first adhesive 238a forms the first bonds 230 in the elastic laminate 200 that bond the first corrugated substrate 202c, the second substrate 204, and the elastic strands 208 together. In particular, the first bonds 230 are intermittently spaced along the machine direction MD and bond discrete lengths of the stretched elastic strands 208 with the first corrugated substrate 202c and the second substrate 204.

As shown in FIG. 4B, the converting apparatus 300 may also include a second adhesive applicator device 330b and/or a third adhesive applicator device 330c. The second adhesive applicator device 330b may be adapted to apply a second adhesive 238b to the first substrate 202. For example, the second adhesive applicator device 330b may operate to apply the second adhesive 238b intermittently to the first corrugated substrate 202c advancing on the second corrugating roll 308a. In some configurations, the second adhesive applicator device 330b may apply the second adhesive 238b to the depressions 236 of the first corrugated substrate 202c without applying the second adhesive 238b to the ridges 234 of the first corrugated substrate 202c. The third adhesive applicator device 330c may be adapted to apply a third adhesive 238c to the second substrate 204. For example, the third adhesive applicator device 330c may operate to apply the third adhesive 238c intermittently to the second substrate 204 before advancing to the combining nip 304. In some configurations, the third adhesive applicator device 330c may apply the third adhesive 238c to the second substrate 204 intermittently along the machine direction MD in locations that correspond with depressions 236 of the first corrugated substrate 202c.

Figure 13B:
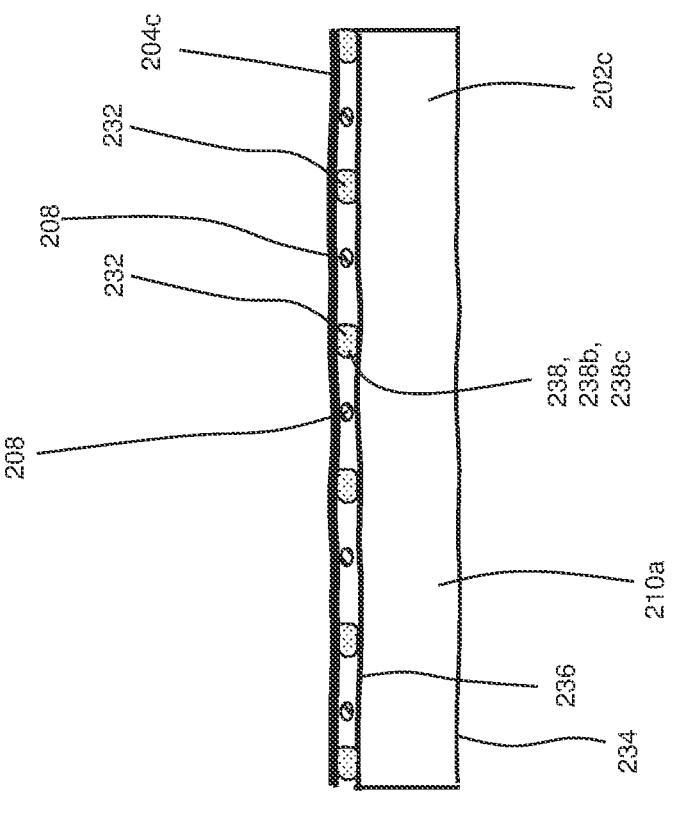
FIG. 13B is a view of the elastic laminate taken along section 13B-13B in FIG. 13.
Figure 13A:
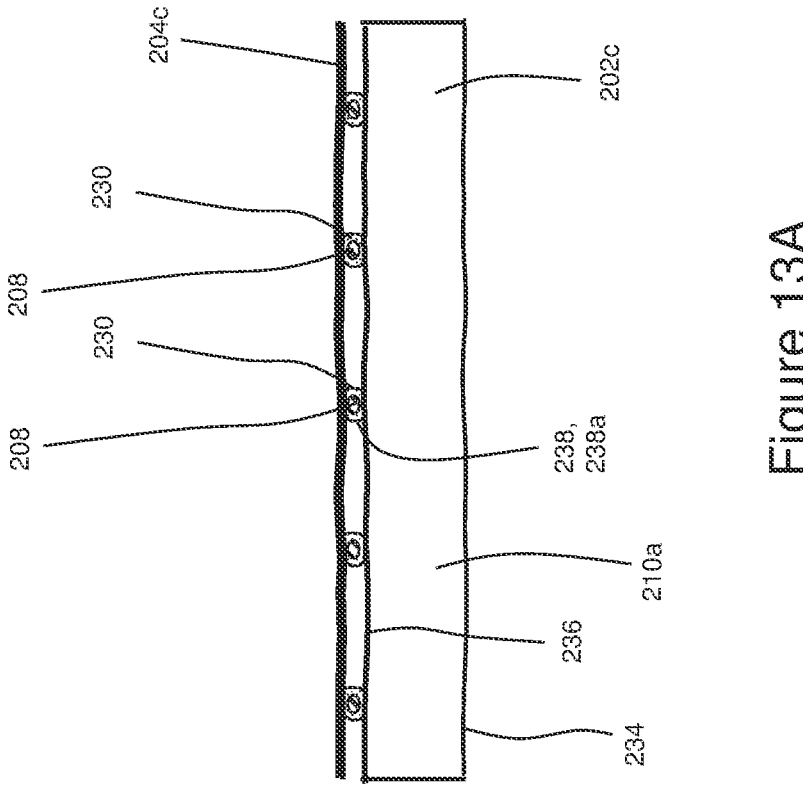
FIG. 13A is a view of the elastic laminate taken along section 13A-13A in FIG. 13.

As shown in FIGS. 13 and 13B, the second adhesive 238b and/or the third adhesive 238c may form the second bonds 232 in the elastic laminate 200 that bond the first corrugated substrate 202c with the second corrugated substrate 204c. In particular, the second bonds 232 may be intermittently spaced along the machine direction MD and bond the depressions 236 of the first corrugated substrate 202c together with the second substrate 204. The second bonds 232 may also be intermittently spaced along the cross direction CD. The elastic strands 208 may extend through and between the second bonds 232. Thus, as the elastic laminate 200 is stretched and retracted, the elastic strands 208 may correspondingly retract and stretch without being significantly inhibited by the second bonds 232. In contrast to the second bonds 232, discrete lengths of elastic strands 208 are anchored with the first corrugated substrate 202c and the second substrate 204 by the first bonds 230. As such, the anchored discrete lengths of elastic strands 208 will move along with the portions of the first corrugated substrate 202c and the second substrate 204 bonded with the first bonds 230 as the elastic laminate 200 is stretched and retracted, as shown in FIGS. 15 and 16.

Figure 16:
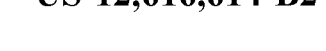
FIG. 16 is a perspective view of the elastic laminate of FIG. 15 in a contracted state.

With continued reference to FIGS. 4B, 15, and 16, the second substrate 204 is not corrugated before being combined with the first corrugated substrate 202c and the elastic strands 208 at the combining nip 304. As such, the second substrate 204 may be in a substantially flattened state when the elastic laminate 200 is fully stretched, as shown in FIG. 15. However, as shown in FIG. 16, as the elastic laminate 200 contracts from a fully stretched state, the second substrate 204 may buckle and/or bend between locations of the first bonds 230 and the second bonds 232 to form corrugations 210*b* defined by alternating ridges 234 and depressions 236.

Figure 14:
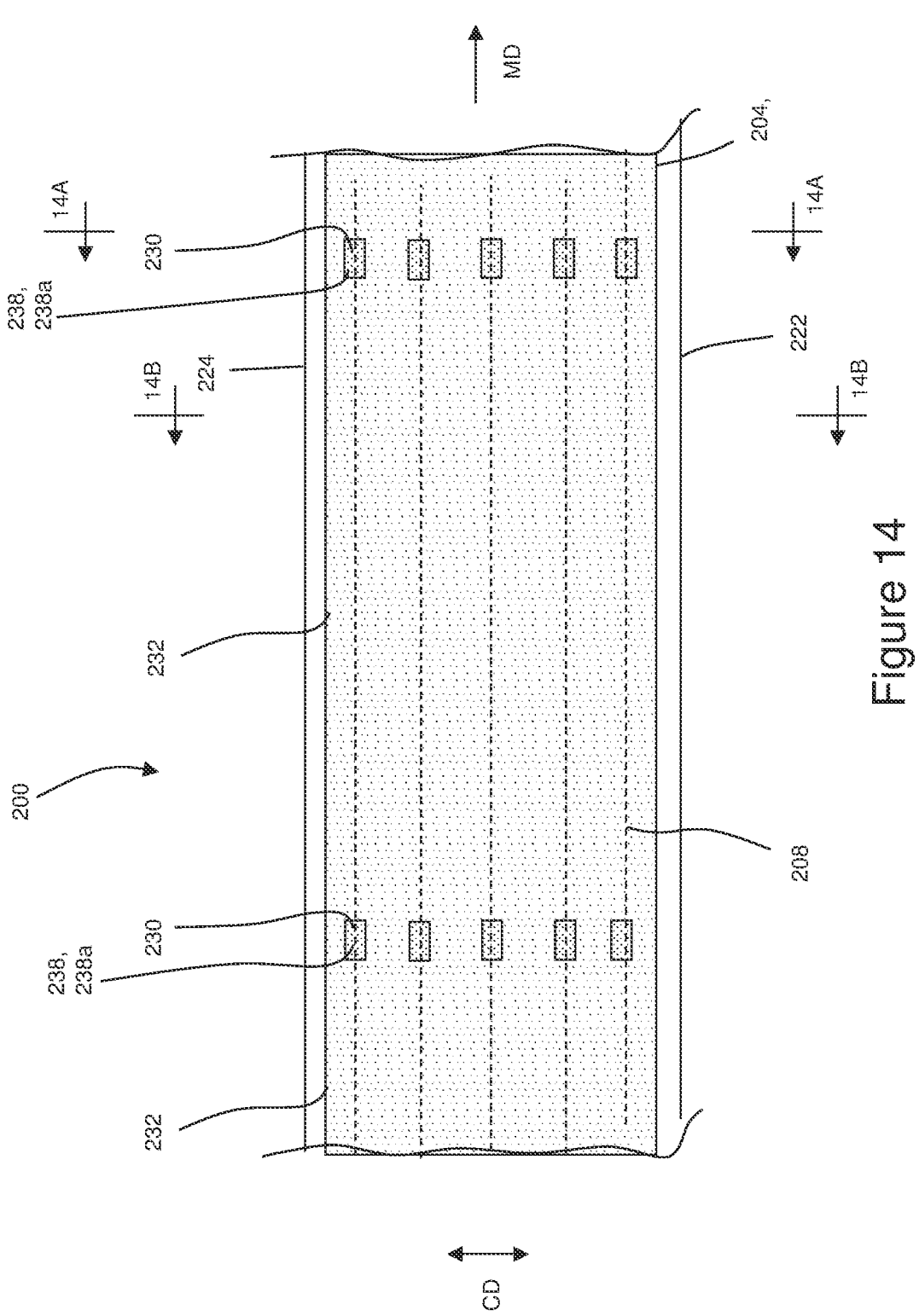
FIG. 14 is a view of an elastic laminate taken along section 14-14 in FIGS. 4B and 4C.
Figure 14B:
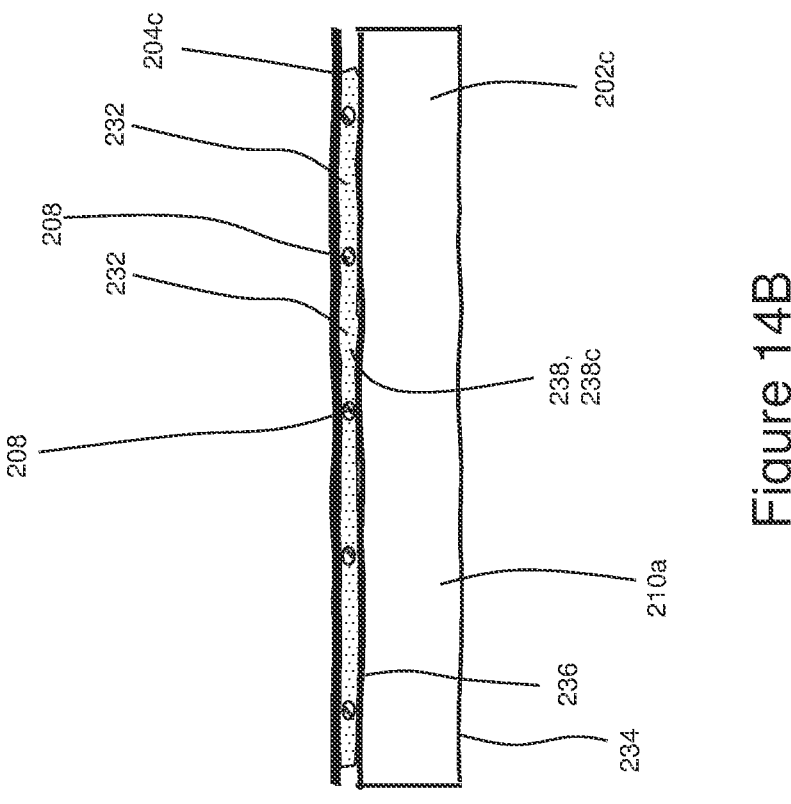
FIG. 14B is a view of the elastic laminate taken along section 14B-14B in FIG. 14.
Figure 14A:
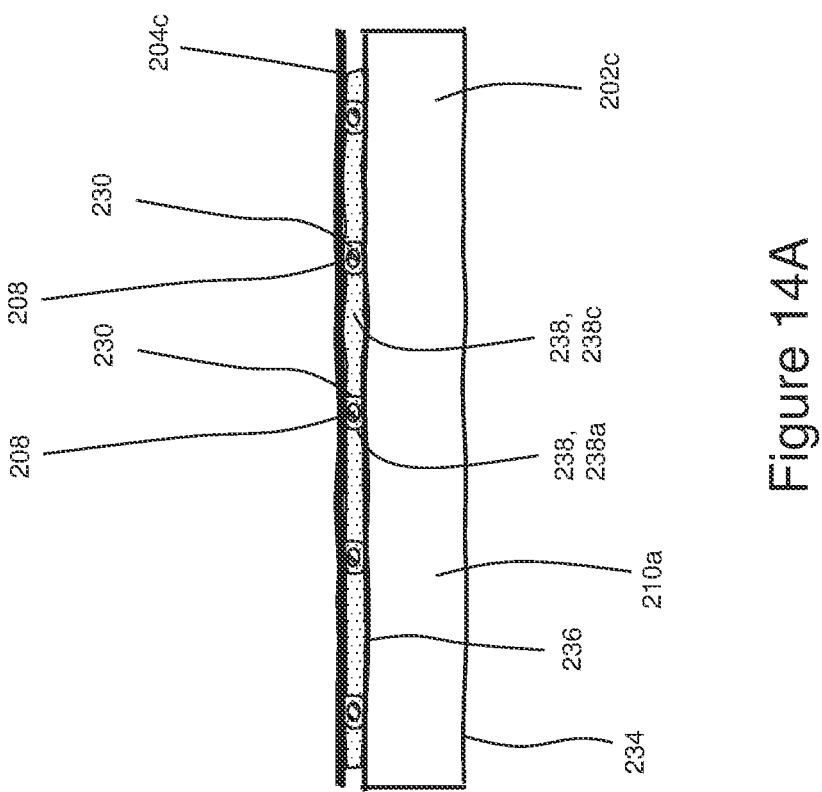
FIG. 14A is a view of the elastic laminate taken along section 14A-14A in FIG. 14.

Although the third adhesive 238*c* is described above in FIG. 4B as being applied intermittently on the second substrate 204, it is to be appreciated that the third adhesive 238*c* may be applied in different ways. For example, as shown in FIGS. 14, 14A, and 14B, the third adhesive 238*c* may be applied continuously along the machine direction MD and/or the cross direction CD of the second substrate 204. Although the third adhesive 238*c* extends continuously along the machine direction MD of the second substrate 204, the intermittent pressing by protrusions 324 of the second corrugating roll 308 against the outer circumferential surface 334 of the anvil roll 332 at the combining nip 304 forms second bonds 232 that are intermittently spaced along the machine direction MD. In addition, although the elastic strands 208 may extend through the third adhesive 238*c* between the depressions 236 of the first corrugated substrate 202*c* and the second substrate 204, the third adhesive may be configured and/or applied to as to allow the elastic strands 208 to retract and stretch without being significantly inhibited by the second bonds 232.

As discussed above, it is to be appreciated that the first adhesive 238*a*, the second adhesive 238*b*, and/or the third adhesive 238*c* may be the same adhesives or different adhesives. In addition, the first adhesive 238*a*, the second adhesive 238*b*, and/or the third adhesive 238*c* may be applied with the same basis weights or different basis weights. For example, the first adhesive 238*a* may be applied with a first basis weight, the second adhesive 238*b* may be applied with a second basis weight, and/or the third adhesive 238*c* may be applied with a third basis weight. In some configurations, the second basis weight and/or the basis weight may be less than the first basis weight.

It is to be appreciated that the corrugating rolls 306, 308 shown in FIG. 4B may also be configured as gears 342 such as described above with reference to FIG. 4A1. As such, the gear teeth 344 of the first corrugating roll 306 and the gear teeth 344 of the second corrugating roll 308 may intermesh at the corrugating nips 310, 312 to form corrugations in the first and/or second substrates 202, 204, such as described above with reference to FIG. 4B. In addition, outer radial surfaces 346 of the second corrugating roll 308 may be in opposing relationships with the outer circumferential surface of 334 of the anvil roll 332 to press the first substrate 202, the second substrate 204, and the elastic strands 208 together at the combining nip 304, such as described above with reference to FIG. 4B.

As discussed above with reference to FIG. 4A, it is also to be appreciated that the second bonds 232 formed by the apparatus 300 of FIG. 4B may be adhesive bonds and/or mechanical bonds. For example, the converting apparatus 300 shown in FIG. 4B may be configured to mechanically bond the first corrugated substrate 202*c* with the second substrate 204 to form the second bonds 232. In some configurations, the second corrugating roll 308 of the corrugating device 302 and the anvil roll 332 may be adapted to mechanically bond the depressions 234 of the first corrugated substrate 202*c* with the second substrate 204 at the combining nip 304.

For example, the second corrugating roll 308 of FIG. 4B may be configured to include bonding elements 348 positioned on the protrusions 324 or gear teeth 344, as described above with reference to FIG. 4A2. As the second corrugating roll 308 and the anvil roll 332 rotate, the elastic laminate 200 is advanced between the pressing surfaces 350 and the outer circumferential surface 334 of the anvil roll 332 to mechanically bond or weld the first corrugated substrate 202*c* and the second substrate 204 together to create the second bonds 232 between the depressions 234 of the first corrugated substrate 202*c* and the second substrate 204. Heat and/or pressure between the pressing surfaces 350 of the protrusions 324 of the second corrugating roll 308 and the outer circumferential surface 334 of the anvil roll 332 may melt and bond the first corrugated substrate 202*c* and second substrate 204 together in areas supported by the pressing surfaces 350 of the protrusions 324 on the second corrugating roll 308. In another example, the anvil roll 332 may be configured to include bonding elements 348 with pressing surfaces 350 positioned on the outer circumferential surface 344, such as shown in FIG. 4B2. In turn, heat and/or pressure between the pressing surfaces 350 of the second anvil roll 332 and the outer radial surfaces 346 of the protrusions 324 or gear teeth 344 of the second corrugating roll 308 may melt and bond the first corrugated substrate 202*c* and second substrate 204 together in areas supported by the pressing surfaces 350 on the anvil roll 332. As such, the second bonds 232 may have shapes that correspond with and may mirror shapes of the pressing surfaces. In some configurations, the second corrugating roll 308 of the corrugating device 302 and/or the anvil roll 332 may also be heated. It is also to be appreciated that the second corrugating roll 308 and anvil roll 324 and/or protrusions 324 and outer circumferential surface 334 may be configured to apply heat and pressure in various ways to perform mechanical bonding, such as for example, the mechanical bonding devices and methods disclosed in in U.S. Pat. Nos. 4,854,984; 6,248,195; 8,778,127; 9,005,392; 9,962,297; and 10,052,237, all of which are incorporated by reference herein.

In another configuration, the converting apparatus 300 of FIG. 4B may be adapted to create second bonds 232 in the form of ultrasonic bonds. For example, the converting apparatus 300 of FIG. 4C includes an energy transfer surface 338 of an ultrasonic bonding device 340. The energy transfer surface 338 is adjacent the second corrugating roll 308 to form a combining nip 304. As such, the combing nip 304 defined between the ultrasonic bonding device 340 and the corrugating device 302 may be characterized as a second metering device 301*b*, as discussed above. The ultrasonic bonding device 340 may include a horn 342 and may be configured to impart ultrasonic energy to the elastic laminate 200 on the second corrugating roll 308 to create the second bonds 232 at the combining nip 304. It is to be appreciated that aspects of the ultrasonic bonding device 340 may be configured in various ways, such as for example linear or rotary type configurations, and such as disclosed for example in U.S. Pat. Nos. 3,113,225; 3,562,041; 3,733,238; 5,110,403; 6,036,796; 6,508,641; and 6,645,330, all of which are incorporated by reference herein. In some configurations, the ultrasonic bonding device 340 may be configured as a linear oscillating type sonotrode, such as for example, available from Herrmann Ultrasonic, Inc. In some configurations, the sonotrode may include a plurality of sonotrodes nested together in the cross direction CD.

It is to be appreciated that the energy transfer surface 338 of the ultrasonic bonding device 340 and the protrusions 324 of the second corrugating roll 308 may be configured in various ways to interact at the combining nip 304 to create the second bonds 232. For example, the energy transfer surface 338 may be configured as flat surface and the second corrugating roll 308 may be configured to include bonding elements 348 positioned on the protrusions 324 or gear teeth 344, as described above with reference to FIG. 4A2. As the second corrugating roll 308 rotates, the elastic laminate 200 is advanced between the pressing surfaces 350 on the protrusions 324 or gear teeth 344 and the energy transfer surface 338 to mechanically bond or weld the first corrugated substrate 202c and the second substrate 204 together to create the second bonds 232 between the depressions 234 of the first corrugated substrate 202c and the second substrate 204. In another example, the energy transfer surface 338 of the ultrasonic bonding device 340 may include raised lands 352, such as shown in FIG. 4C1. Thus, as the second corrugating roll 308 rotates, the elastic laminate 200 is advanced between the outer radial surfaces 346 of the protrusions 324 or gear teeth 344 and the raised lands 352 of the energy transfer surface 338 to mechanically bond or weld the first corrugated substrate 202c and the second substrate 204 together to create the second bonds 232 between the depressions 234 of the first corrugated substrate 202c and the second substrate 204.

With further regard to incorporating the elastic laminates 200 herein into various diaper assembly processes, it is also to be appreciated that the first bonds 230 and second bonds 232 discussed herein with reference to the accompanying figures may be configured in various ways. For example, the first bonds 230 may be configured as anchoring bonds, and the second bonds 232 may be configured as trapping bonds or guiding bonds. More particularly, the anchoring bonds may be configured to anchor and bond discrete lengths of the stretched elastic strands 208 with and between the first substrate 202 and the second substrate 204, and the trapping bonds may be configured to bond the first and second substrates 202, 204 directly to each other, wherein the trapping bonds may be separated from each other in a cross direction by at least one elastic strand 208, and as such, the elastic strands 208 may be trapped between the trapping bonds. In some configurations, the trapping bonds may be arranged to bond the first and second substrates 202, 204 directly together without adhering the elastic strands 208 to either substrate. As such, the trapping bonds may be configured to trap and immobilize discrete lengths of the elastic strands 208 between the trapping bonds after the elastic strands 208 have contracted, such as disclosed for example, in U.S. Pat. No. 6,291,039 and U.S. Patent Publication Nos. 2016/0331600 A1; 2018/0168880 A1; 2018/0170027 A1; and 2018/0168879 A1, all of which are incorporated by reference herein.

Figure 17:
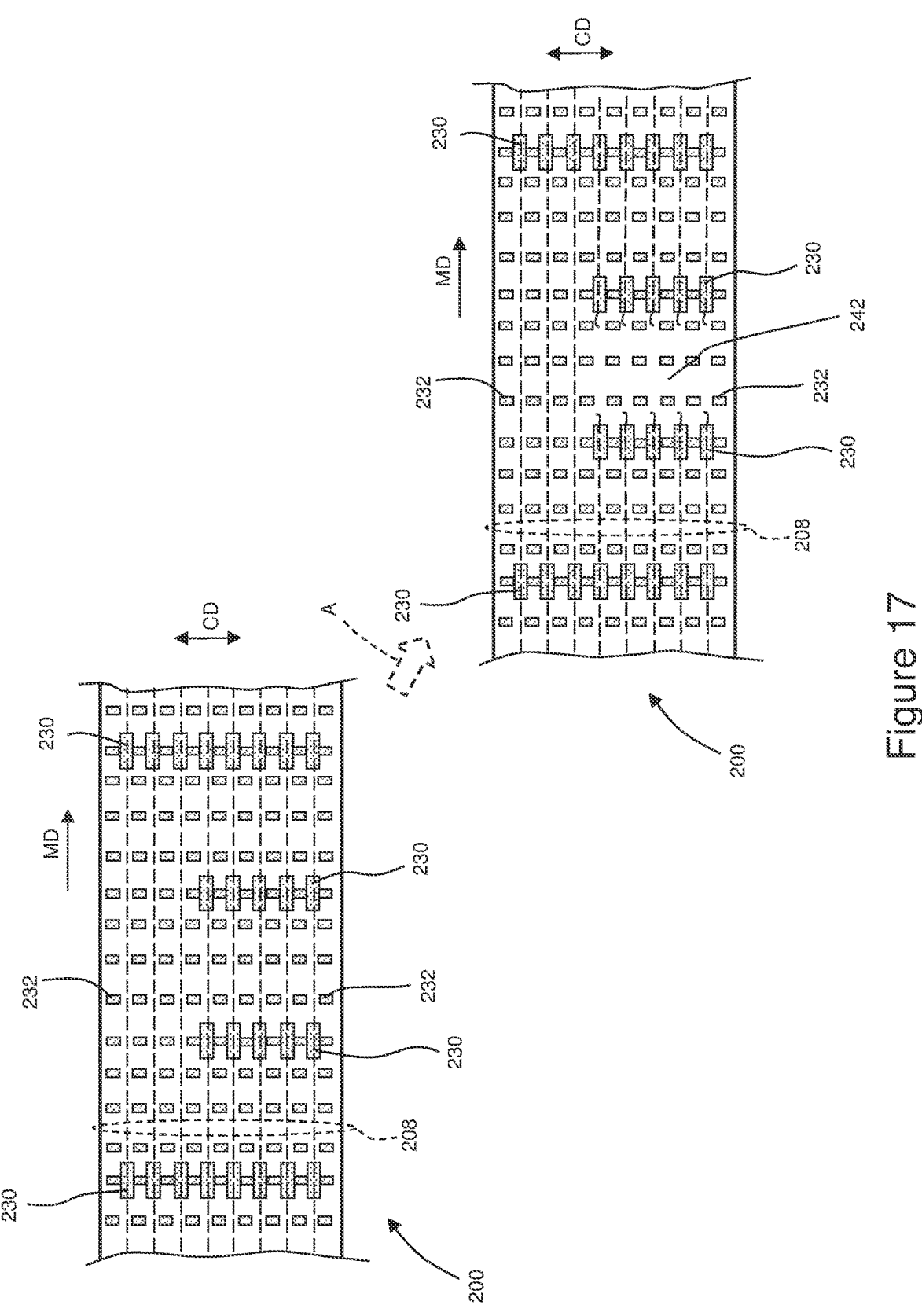
FIG. 17 is a schematic view of a tummy elastic cutting process.

It is also to be appreciated that the elastic laminates 200 herein may be configured to be subjected to various elastic strand cutting processes, sometimes referred to as tummy elastic cutting, to create deactivated regions 242 in the elastic laminate positioned along the machine direction MD between elasticized regions by severing at least one stretched elastic strand 208, wherein the at least one severed elastic strand 208 retracts to at least one anchor bond 230. For example, as shown in FIG. 17, elastic strands 208 may be severed between anchoring bonds 230 in an elastic laminate 200, and as such, the severed elastic strands 208 may retract to the anchoring bonds 230 (represented by the dashed arrow "A") to form deactivated regions 242. In some assembly operations, absorbent chassis 102 may be connected with the elastic laminate 200 in such deactivated regions 242. As such, it also to be appreciated that the methods and apparatuses herein may be adapted to operate with various types of absorbent article assembly processes that may incorporate elastic laminates assembled thereby, such as disclosed for example in U.S. Pat. Nos. 8,186,296; 9,265,672; 9,248,054; and 9,730,839 and U.S. Patent Publication Nos. 2013/0255861 A1; 2013/0255862 A1; 2013/

0255863 A1; 2013/0255864 A1; 2013/0255865 A1; 2018/0169964 A1; and 2018/0168879 A1, all of which are incorporated by reference herein. In other examples, the elastic laminates 200 herein may be used to construct various types of leg cuff, backsheet, and/or topsheet configurations. In yet other examples, the elastic laminates may be used to construct waistbands and/or side panels in taped diaper configurations.

Figure 18:
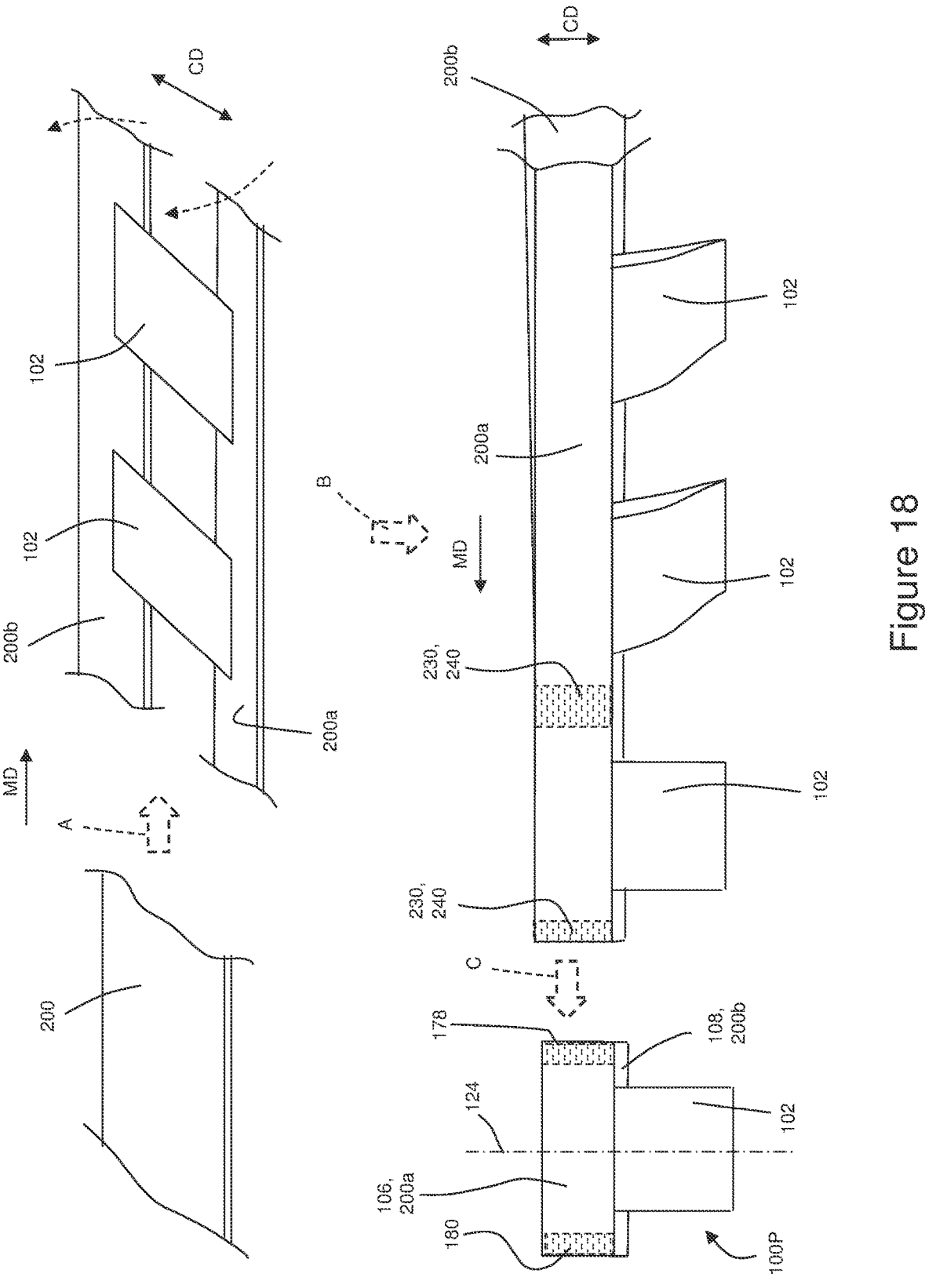
FIG. 18 is a schematic view of a diaper pant assembly process.

As described above, it is to be appreciated that the elastic laminates 200 herein can be used to construct various types of absorbent article components. For example, the elastic laminates 200 may be used as a continuous length of elastomeric belt material that may be converted into the first and second elastic belts 106, 108 discussed above with reference to FIGS. 1-3B. As such, the elastic material 206 may correspond with the belt elastic material 168 interposed between the outer layer 162 and the inner layer 164, which in turn, may correspond with either the first and/or second substrates 202, 204. For example, as shown in FIG. 18, when assembling diaper pants 100P, the elastic laminate 200 may be converted into a first elastic belt laminate 200a and/or a second elastic belt laminate 200b (represented by the dashed arrow "A"). The first elastic belt laminate 200a and the second elastic belt laminate 200b may be separated from each other in the cross direction CD and may be connected with each other with a plurality of chassis 102 intermittently spaced along the machine direction MD. During subsequent assembly operations, the chassis 102 may be folded (represented by the dashed arrow "B") so as to position the first elastic belt laminate 200a into a facing relationship with the second elastic belt laminate 200b. Bonds 240 may be applied to the overlapping belt laminates 200a, 200b. It is also to be appreciated that anchoring bonds 230 may also be located in regions where the bonds 240 are located. Subsequently, discrete diaper pants 100P may be formed by separating the first and second belt laminates 200a, 200b into first and second belts 106, 108 by cutting along the cross direction CD through the first and second belt laminates 200a, 200b at the bonds 240 and anchoring bonds 230 (represented by the dashed arrow "C"). As such, the bonds 240 may be divided to define the first and second side seams 178, 180, respectively. It is also to be appreciated that the elastic laminates 200 converted into the first and second elastic belts 106, 108 may be subjected to other types of cutting operations, such as leg cut out or contouring cutting operations, such as disclosed for example in U.S. Pat. No. 10,098,792, which is incorporated by reference. As such, the laminates 200 may be configured to locate the anchoring bonds 230 where the cutting operations occur to help ensure the elastic strands are held in place after the laminate has been cut. In some configurations, the elastic laminates herein may be converted to define the first and second elastic belts 106, 108 described herein and may also be converted to define one or more components of multi-component belt assemblies, such as disclosed in U.S. Patent Publication No. 2022/0142828 A1, which is incorporated by reference.
Combinations A1. A method for making an elastomeric laminate, the method comprising steps of: providing a first corrugated substrate by forming ridges that alternate with depressions along a machine direction in a first substrate; providing a second corrugated substrate by forming ridges that alternate with depressions along the machine direction in a second substrate; advancing elastic strands in the machine direction; stretching the elastic strands in the machine direction; subsequent to the step of stretching the elastic strands, applying a first adhesive intermittently to the elastic strands to form discrete regions of the first adhesive on the elastic strands; bonding discrete lengths of the elastic strands with and between the first corrugated substrate and the second corrugated substrate with first bonds formed with the discrete regions of the first adhesive; and bonding the depressions of first corrugated substrate directly with the depressions of the second corrugated substrate with second bonds along the machine direction between consecutive first bonds.

A2. The method of paragraph A1, wherein elastic strands extend through the second bonds and wherein the elastic strands can retract and stretch through the second bonds.

A3. The method of either paragraph A1 or A2, wherein the second bonds comprise a second adhesive.

A4. The method of paragraph A3, further comprising a step of applying the second adhesive to at least one of the first corrugated substrate and the second corrugated substrate.

A5. The method of paragraph A4, wherein the step of applying the second adhesive to at least one of the first corrugated substrate and the second corrugated substrate further comprises applying the second adhesive to the depressions of at least one of the first corrugated substrate and the second corrugated substrate.

A6. The method of either paragraph A4 or A5, wherein the first adhesive is applied with a first basis weight and wherein the second adhesive is applied with a second basis weight, and wherein the second basis weight is less than the first basis weight.

A7. The method of any of paragraphs A4-A6, wherein the second adhesive is positioned between the elastic strands and at least one of the first corrugated substrate and the second corrugated substrate without adhering the elastic strands to the at least one of the first corrugated substrate and the second corrugated substrate.

A8. The method of any of paragraphs A1-A7, wherein the second bonds comprise mechanical bonds.

A9. The method of paragraph A8, wherein the mechanical bonds comprise ultrasonic bonds.

A10. The method of paragraph A8, wherein the mechanical bonds comprise heat or pressure bonds.

A11. The method of any of paragraphs A1-A10, wherein the step of stretching comprises advancing the elastic strands from a first metering device at a first speed to a second metering device at a second speed, wherein the second speed is greater than the first speed.

A12. The method of paragraph A11, wherein the first metering device comprises individual spools of elastic strands.

A13. The method of paragraph A11, wherein the first metering device comprises a beam with a plurality of elastic strands wound thereon.

A14. The method of paragraph A11, wherein the second metering device comprises a first roller adjacent a second roller defining a nip therebetween, and wherein the elastic strands advance through the nip and are sandwiched between the first corrugated substrate and the second corrugated substrate.

A15. The method of paragraph A14, wherein the first roller is adjacent a third roller, wherein the first roller and third roller each comprise a plurality of protrusions that intermesh when the first roller and the third roller rotate in opposite directions, and wherein the step of providing the first corrugated substrate further comprises advancing the first substrate between the intermeshing protrusions of the first roller and the third roller.

A16. The method of any of paragraphs A1-A15, wherein the elastic strands comprise a decitex less than about 300.

A17. The method of any of paragraphs A1-A16, further comprising a step of separating the elastic strands from each other by about 0.5 mm to about 3 mm in a cross direction.

A18. The method of any of paragraphs A1-A17, further comprising steps of: forming a deactivated region by cutting the elastic strands between consecutive first bonds, wherein cut elastic strands retract to the consecutive anchor bonds; and bonding an absorbent chassis to the deactivated region.

A19. The method of any of paragraphs A1-A18, further comprising steps of: bonding the elastic laminate with a second elastic laminate with side seam bonds, wherein the first bonds are located in regions where the side seam bonds are located; cutting the elastic laminate and the second elastic laminate through the side seam bonds and the first bonds to form discrete diaper pants.

B1. A method for making an elastomeric laminate, the method comprising steps of: providing a first corrugated substrate by forming ridges that alternate with depressions along a machine direction in a first substrate; providing a second substrate, wherein the second substrate is not corrugated; advancing elastic strands in the machine direction; stretching the elastic strands in the machine direction; subsequent to stretching the elastics strands, applying a first adhesive intermittently to the elastic strands to form discrete regions of the first adhesive on the elastic strands; bonding discrete lengths of the elastic strands with and between the first corrugated substrate and the second substrate with first bonds formed with the discrete regions of the first adhesive; and bonding the depressions of first corrugated substrate directly with the second substrate with second bonds along the machine direction between consecutive first bonds.

B2. The method of paragraph B1, wherein elastic strands extend through the second bonds and wherein the elastic strands can retract and stretch through the second bonds.

B3. The method of either paragraph B1 or B2, wherein the second bonds comprise a second adhesive.

B4. The method of paragraph B3, further comprising a step of applying the second adhesive to the first corrugated substrate.

B5. The method of paragraph B3, further comprising a step of applying the second adhesive to the second substrate.

B6. The method of any of paragraphs B2-B5, wherein the first adhesive is applied with a first basis weight and wherein the second adhesive is applied with a second basis weight, and wherein the second basis weight is less than the first basis weight.

B7. The method of any of paragraphs B1-B6, wherein the second bonds comprise mechanical bonds.

B8. The method of paragraph B7, wherein the mechanical bonds comprise ultrasonic bonds.

B9. The method of paragraph B7, wherein the mechanical bonds comprise heat or pressure bonds.

B10. The method of any of paragraphs B1-B9, wherein the step of stretching comprises advancing the elastic strands from a first metering device at a first speed to a second metering device at a second speed, wherein the second speed is greater than the first speed.

B11. The method of paragraph B10, wherein the first metering device comprises individual spools of elastic strands.

B12. The method of paragraph B10, wherein the first metering device comprises a beam with a plurality of elastic strands wound thereon.

B13. The method of paragraph B10, wherein the second metering device comprises a first roller adjacent a second roller defining a nip therebetween, and wherein the elastic strands advance through the nip and are sandwiched between the first corrugated substrate and the second corrugated substrate.

B14. The method of paragraph B13, wherein the first roller is adjacent a third roller, wherein the first roller and third roller each comprise a plurality of protrusions that intermesh when the first roller and the third roller rotate in opposite directions, and wherein the step of providing the first corrugated substrate further comprises advancing the first substrate between the intermeshing protrusions of the first roller and the third roller.

B15. The method of any of paragraphs B1-B14, wherein the elastic strands comprise a decitex less than about 300.

B16. The method of any of paragraphs B1-B15, further comprising a step of separating the elastic strands from each other by about 0.5 mm to about 3 mm in a cross direction.

C1. A method for making an elastomeric laminate, the method comprising steps of: providing a first substrate and a second substrate; corrugating at least one of the first substrate and the second substrate by forming ridges that alternate with depressions along a machine direction in at least one of the first substrate and the second substrate; advancing elastic strands in the machine direction; stretching the elastic strands in the machine direction; bonding discrete lengths of the elastic strands with and between the first substrate and the second substrate with first bonds; and bonding the first substrate directly with the second substrate with second bonds along the machine direction between consecutive first bonds.

C2. The method of paragraph C1, further comprising a step of applying a first adhesive intermittently to the elastic strands to form discrete regions of the first adhesive on the elastic strands, and wherein the first bonds are formed with the discrete regions of the first adhesive, and wherein the second bonds comprise a second adhesive.

C3. The method of paragraph C2, further comprising a step of applying the second adhesive to at least one of the first substrate and the second substrate.

C4. The method of paragraph C3, wherein the first adhesive is applied with a first basis weight and wherein the second adhesive is applied with a second basis weight, and wherein the second basis weight is less than the first basis weight.

C5. The method of paragraph C4, further comprising a step of applying a first adhesive intermittently to the elastic strands to form discrete regions of the first adhesive on the elastic strands, and wherein the first bonds are formed with the discrete regions of the first adhesive, and wherein the second bonds comprise mechanical bonds.

C6. The method of paragraph C5, wherein the mechanical bonds comprise ultrasonic bonds.

C7. The method of paragraph C5, wherein the mechanical bonds comprise heat or pressure bonds.

C8. The method of any of paragraphs C1-C7, wherein the first bonds comprise mechanical bonds and wherein the second bonds comprise at least one of adhesive bonds and mechanical bonds.

C9. The method of paragraph C8, wherein the first bonds further comprise adhesive.

D1. An elastomeric laminate comprising: a first substrate; a second substrate, wherein at least one of the first substrate and the second substrate is corrugated; elastic strands positioned between the first substrate and the second substrate; wherein discrete lengths of the elastic strands are bonded with the first substrate and the second substrate with first bonds; wherein the first substrate and the second substrate are bonded directly with each other with second bonds positioned between consecutive first bonds; and wherein the elastic strands extend through the second bonds and the elastic strands can retract and stretch through the second bonds.

D2. The elastomeric laminate of paragraph D1, wherein the first bonds comprise discrete regions of a first adhesive on the elastic strands.

D3. The elastomeric laminate of paragraph D2, wherein the second bonds comprise a second adhesive on at least one of the first substrate and the second substrate.

D4. The elastomeric laminate of paragraph D2, wherein the second bonds comprise mechanical bonds.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making an elastomeric laminate, the method comprising steps of:
providing a first corrugated substrate by forming ridges that alternate with depressions along a machine direction in a first substrate;
providing a second corrugated substrate by forming ridges that alternate with depressions along the machine direction in a second substrate;
advancing elastic strands in the machine direction;
stretching the elastic strands in the machine direction;
subsequent to the step of stretching the elastic strands, applying a first adhesive intermittently to the elastic strands to form discrete regions of the first adhesive on the elastic strands;
bonding discrete lengths of the elastic strands with and between the first corrugated substrate and the second corrugated substrate with first bonds formed with the discrete regions of the first adhesive; and
bonding the depressions of the first corrugated substrate directly with the depressions of the second corrugated substrate with second bonds along the machine direction between consecutive first bonds.

2. The method of claim 1, wherein the elastic strands extend through the second bonds and wherein the elastic strands can retract and stretch through the second bonds.

3. The method of claim 1, wherein the second bonds comprise a second adhesive.

4. The method of claim 3, further comprising a step of applying the second adhesive to at least one of the first corrugated substrate and the second corrugated substrate.

5. The method of claim 4, wherein the step of applying the second adhesive to at least one of the first corrugated substrate and the second corrugated substrate further comprises applying the second adhesive to the depressions of at least one of the first corrugated substrate and the second corrugated substrate.

6. The method of claim 4, wherein the first adhesive is applied with a first basis weight and wherein the second adhesive is applied with a second basis weight, and wherein the second basis weight is less than the first basis weight.

7. The method of claim 4, wherein the second adhesive is positioned between the elastic strands and at least one of the first corrugated substrate and the second corrugated substrate without adhering the elastic strands to the at least one of the first corrugated substrate and the second corrugated substrate.

8. The method of claim 1, wherein the second bonds comprise mechanical bonds.

9. The method of claim 8, wherein the mechanical bonds comprise ultrasonic bonds.

10. The method of claim 8, wherein the mechanical bonds comprise heat or pressure bonds.

11. The method of claim 1, wherein the step of stretching comprises advancing the elastic strands from a first metering device at a first speed to a second metering device at a second speed, wherein the second speed is greater than the first speed.

12. The method of claim 11, wherein the first metering device comprises individual spools of elastic strands.

13. The method of claim 11, wherein the first metering device comprises a beam with a plurality of elastic strands wound thereon.

14. The method of claim 11, wherein the second metering device comprises a first roller adjacent a second roller defining a nip therebetween, and wherein the elastic strands advance through the nip and are sandwiched between the first corrugated substrate and the second corrugated substrate.

15. The method of claim 14, wherein the first roller is adjacent a third roller, wherein the first roller and third roller each comprise a plurality of protrusions that intermesh when the first roller and the third roller rotate in opposite directions, and wherein the step of providing the first corrugated substrate further comprises advancing the first substrate between the intermeshing protrusions of the first roller and the third roller.

16. The method of claim 1, wherein the elastic strands comprise a decitex less than about 300.

17. The method of claim 1, further comprising a step of separating the elastic strands from each other by about 0.5 mm to about 3 mm in a cross direction.

18. The method of claim 1, further comprising steps of:
forming a deactivated region by cutting the elastic strands between consecutive first bonds, wherein cut elastic strands retract to the consecutive first bonds; and
bonding an absorbent chassis to the deactivated region.

19. The method of claim 1, further comprising steps of:
bonding the elastomeric laminate with a second elastomeric laminate with side seam bonds, wherein the first bonds are located in regions where the side seam bonds are located; and
cutting the elastomeric laminate and the second elastomeric laminate through the side seam bonds and the first bonds to form discrete diaper pants.

\* \* \* \* \*